(12) United States Patent
Burrows et al.

(10) Patent No.: US 10,923,223 B2
(45) Date of Patent: Feb. 16, 2021

(54) DATA-ENABLED SYRINGE COLLECTION CONTAINER AND SYSTEMS USING SAME

(71) Applicant: DoseCue, LLC, Philadelphia, PA (US)

(72) Inventors: Mark Burrows, Philadelphia, PA (US); Barbara Dove, Philadelphia, PA (US); Ed Hawley, Keyport, NJ (US)

(73) Assignee: DOSECUE, LLC, Philadelphia, PA (US)

( * ) Notice: Subject to any disclaimer, the term of this patent is extended or adjusted under 35 U.S.C. 154(b) by 6 days.

(21) Appl. No.: 16/452,013

(22) Filed: Jun. 25, 2019

(65) Prior Publication Data

US 2020/0005925 A1    Jan. 2, 2020

Related U.S. Application Data

(60) Provisional application No. 62/690,678, filed on Jun. 27, 2018.

(51) Int. Cl.
| | | |
|---|---|---|
| *G07G 1/00* | (2006.01) | |
| *G16H 20/17* | (2018.01) | |
| *A61M 5/172* | (2006.01) | |
| *A61M 5/315* | (2006.01) | |
| *A61M 5/20* | (2006.01) | |

(52) U.S. Cl.
CPC ............ *G16H 20/17* (2018.01); *A61M 5/172* (2013.01); *A61M 5/31525* (2013.01); *A61M 5/20* (2013.01); *A61M 2205/3592* (2013.01); *A61M 2205/52* (2013.01)

(58) Field of Classification Search
CPC ........ G16H 20/13; G16H 10/00; G16H 20/17; G06F 19/34

USPC ........................................................ 235/451
See application file for complete search history.

(56) References Cited

U.S. PATENT DOCUMENTS

| | | | | |
|---|---|---|---|---|
| 6,283,909 B1* | 9/2001 | Sharp | ................... | A61B 50/362 206/366 |
| 7,694,811 B2* | 4/2010 | Brown | ................... | B65D 5/722 206/366 |
| 7,789,230 B2* | 9/2010 | Klein | ................... | A61B 50/362 206/366 |
| 8,770,479 B1* | 7/2014 | Shoenfeld | ........... | G06F 19/3462 235/385 |
| 10,321,968 B2* | 6/2019 | Burgess | ................ | A61B 50/36 |
| 2006/0192001 A1* | 8/2006 | Shaffer | ................ | G06Q 10/087 235/385 |

(Continued)

*Primary Examiner* — Ahshik Kim
(74) *Attorney, Agent, or Firm* — Ward and Smith, P.A.; Ryan K. Simmons

(57) ABSTRACT

A data-enabled syringe collection container. The data-enabled syringe collection container may include an upper inlet body; a container body coupled to the upper inlet body; an electronics module configured for sensing and tracking dose events, the electronics module coupled to at least one of the upper inlet body or the container body; and wherein the upper inlet body may include an inlet lid; a first opening; an entry channel; and a receiving assembly including a dropout door, and wherein the inlet lid is configured for covering and accessing the first opening, the entry channel is configured to provide a passage way from the first opening to the receiving assembly, and the dropout door is configured to allow passage through a second opening into the container body.

27 Claims, 23 Drawing Sheets

(56) References Cited

U.S. PATENT DOCUMENTS

| | | | | |
|---|---|---|---|---|
| 2008/0237341 A1* | 10/2008 | Fleck | .................... | A61B 50/10 235/385 |
| 2014/0197954 A1* | 7/2014 | Caputo | .................. | G06F 19/30 340/572.1 |
| 2015/0164590 A1* | 6/2015 | Sakihama | ........... | A61M 5/3205 206/366 |
| 2015/0332209 A1* | 11/2015 | DeBusk | ............... | G06Q 10/087 705/2 |

* cited by examiner

DATA-ENABLED SYRINGE COLLECTION CONTAINER AND SYSTEMS USING SAME

CROSS-REFERENCE TO RELATED APPLICATIONS

This application is related and claims priority to U.S. Pat. App. Ser. No. 62/690,678, entitled "Data-Enabled Syringe Collection Container and System Using Same," filed on Jun. 27, 2018, the disclosure of which is incorporated herein by reference in its entirety.

The presently disclosed subject matter, further, is related to U.S. Pat. No. 9,514,282, entitled "Data-enabled pharmaceutical container and methods for using same," issued on Dec. 6, 2016; U.S. Pat. No. 9,460,265, entitled "Data-enabled pharmaceutical container and methods for using same," issued on Oct. 4, 2016; U.S. Patent Pub. No. 20140052468, entitled "Medication Adherence System for and Method of Monitoring a Patient Medication Adherence and Facilitating Dose Reminders," published on Feb. 20, 2014; and U.S. Patent Pub. No. 20150254427, entitled "Medication Adherence System for and Method of Monitoring a Patient Medication Adherence and Facilitating Dose Reminders," published on Sep. 10, 2015; the entire disclosures of which are incorporated herein by reference.

FIELD OF THE INVENTION

The presently disclosed subject matter relates generally to the field of medication adherence and more particularly to a data-enabled syringe collection container and systems for monitoring a patient's medication adherence with respect to self-inject medications and facilitating dose-reminder and/or dose-taken notifications.

BACKGROUND

Outpatient prescription medication treatments are relied upon heavily for increased quality of life and lower lifetime healthcare costs. Medical experts have long held that taking at least 80% of a prescribed drug is required to achieve desired therapeutic outcomes and lower lifetime healthcare costs. For example, a patient who faithfully takes cholesterol-reducing medicine significantly reduces the likelihood of a coronary event that has attendant cost-intensive medical procedures and diminished quality of life. Outpatients strongly desire to avoid such events and hospital stays, yet only 20% of all outpatients take their oral prescription medicines according to doctor's instructions.

Increased medication adherence, also known as patient adherence, medication compliance, or patient compliance, benefits the healthcare system by vastly reducing patients' lifetime medical costs while increasing their therapeutic outcomes. Further, market research suggests that patients have a desire to adhere, but will not take on the burden of any additional actions or otherwise add steps to their dose-taking behavior.

Attempts to date to increase patient adherence have involved attaching dosage-reminder devices to containers by pharmacists, patients, or patient's caregivers. These have had no sustainable impact on adherence, principally because such devices have typically increased, rather than lessened, patients' burden in taking medication. Further, whereas currently attempts have been made to increase patient adherence with respect to oral medication, there have been no such attempts to help patients increase adherence with self-inject medications. For example, there is currently no reliable way to monitor and/or track injectable medication. Hemophilia-advocacy organizations and payers advise patients to keep injection logs or infusion journals to document date and time of injections; yet such record keeping is unreliable because the burden falls on patients. Accordingly, it would be beneficial to develop new approaches for reminding at dose time and monitoring usage of self-inject medications, particularly in light of how expensive injectable medication can be. For example, currently the cost of injectable hemophilia medication ranges from $5,000 to $25,000 per dose.

SUMMARY

In one embodiment, a data-enabled syringe collection container is provided. The data-enabled syringe collection container may include an upper inlet body; a container body coupled to the upper inlet body; and an electronics module configured for sensing and tracking dose events, the electronics module coupled to at least one of the upper inlet body and the container body. The upper inlet body may include an inlet lid; a first opening; an entry channel; and a receiving assembly, wherein the inlet lid may be configured for covering and accessing the first opening, and wherein the entry channel may be configured to provide a passageway from the first opening to the receiving assembly. The receiving assembly comprises a dropout door configured to allow passage through a second opening into the container body. The dropout door may include a spring-loaded one-way door configured to open downward into the container body and to automatically close after an article has passed through. The entry channel may be tapered from a top portion to a bottom portion thereof. The container body may be configured as a reservoir for holding a quantity of spent syringes. The first opening, the entry channel, and the second opening may be configured to allow for a syringe to pass there through. The electronics module may include a control board. The control board may include one or more active and passive electrical and/or mechanical components for sensing one or more of when the inlet lid and/or dropout door is open and closed, a duration and time that the inlet lid and/or dropout door is open, and a physical amount that the inlet lid and/or dropout door is open. The control board may include a processor configured for processing data from the one or more active and passive electrical and/or mechanical components with respect to a patient's dosing regimen and for storing and/or communicating information generated from the processed data. The control board may include any one or more of a communications interface, a processor, a real-time clock, one or more switches, one or more sensors, and one or more indicators. The one or more indicators may include one or more light-emitting diodes (LEDs). The processor may include data storage for storing one or more of a patient's dosing regimen, a dose detection algorithm, actual dose data, and a security component, wherein the processor may be configured to process data from one or more of the real-time clock, the one or more switches, and/or the one or more sensors with respect to a patient's predefined dosing regimen, and for one or more of storing and communicating data about doses taken, doses missed, extra doses, early doses, and/or late doses. The one or more of the real-time clock, the one or more switches, and/or the one or more sensors may be configured to detect one or more of the open or closed state, the time and duration opened, and the degree of openness of one or both of the inlet lid and the dropout door. A dose event may be deemed valid if it is detected that both the inlet lid and the dropout-door are opened and/or closed at substantially the same time. A dose event may be deemed valid if it is detected that both the inlet lid and the dropout-door are open at substantially the same time and any one or more of: that the amount of time that the dropout door is open corresponds to a predefined amount of time; the degree of openness of the dropout door meets a predefined threshold value; and that a time period between successive dropout door openings is greater than a predefined minimum threshold of time. The predefined amount of time that the dropout door is open may be substantially equal to an amount of time that it takes for a spent syringe to pass through the dropout door. The one or more active and passive electrical and/or mechanical components may include a movable lever. A portion of the movable lever may extend through a corresponding opening in an upper edge of the upper inlet body, and may be configured to engage with the inlet lid, wherein the movable lever may be part of a mechanism for detecting an open or closed state of the inlet lid. The movable lever may be configured such that when the inlet lid is closed, the inlet lid is in contact with the movable lever causing the movable lever to be in a first position, and when the inlet lid is open, the inlet lid does not contact the movable lever causing the movable lever to be in a second position. The one or more active and passive electrical and/or mechanical components may further include a momentary contact switch, and wherein the movable lever in one of the first and second positions engages an actuator of the momentary contact switch. The movable lever and the momentary contact switch may provide the mechanism for determining whether the inlet lid is in an opened or closed state, wherein when the inlet lid is closed and in contact with the tip of the movable lever, a portion of the movable lever is pushed against the actuator of the momentary contact switch, and the momentary contact switch is in one state, and when the inlet lid is open and not in contact with the tip of the movable lever, the movable lever is not pushed against the actuator of the momentary contact switch, and the momentary contact switch is in another state. The electronics module may be configured for providing a reminder at dose time, detecting valid dose events, and processing and communicating data about dose events and/or dose exception events. Sensing a valid dose event may include data input from at least two of the one or more switches and/or one or more sensors to coincide with one another. The coinciding at least two data inputs from the one or more switches and/or one or more sensors may include data input indicating the inlet lid and the dropout door are open at substantially the same time. The electronics module may be configured for transmitting data therefrom, via a communications interface, to an external computing device via a wireless network to one or more of a patient, a caretaker, and/or an authorized party via the communications interface, wherein the data may include information regarding an actual dose event. If the information regarding the actual dose event indicates a missed dose according to a patient's dosing regimen the electronics module may be configured to activate one or more indicators to indicate a missed dose, and wherein if the information regarding the actual dose event indicates a valid dose event according to the patient's dosing regimen the electronics module may be configured to activate one or more indicators to indicate a taken dose. The electronics module may further be configured to determine whether a prescription refill is needed based on a number of valid dose events as compared to recorded actual dose data and a patient's dosing regimen, and wherein if it is determined a prescription refill is needed the electronics module may be configured to activate one or more indicators to indicate a prescription refill is needed, and further wherein a prescription refill notice may be sent to one or more of to one or more of a patient, a caretaker, and/or an authorized party via the communications interface.

In another embodiment, a data-enabled device for receiving spent syringes is provided. The data-enabled device for receiving spent syringes may include an inlet body. The inlet body may include an inlet lid; a first opening; an entry channel; a receiving assembly; and wherein the inlet lid may be configured for covering and accessing the first opening, and wherein the entry channel may be configured to provide a passage way from the first opening to the receiving assembly, and wherein the receiving assembly comprises a dropout door configured to allow passage through a second opening, and further wherein the first opening, the entry channel, the receiving assembly, and the second opening are configured to allow a spent syringe to pass there through. The data-enabled device for receiving spent syringes may further include an electronics module configured for sensing and tracking dose events, wherein the electronics module may be coupled to the inlet body.

In yet another embodiment, a method of determining a valid dose event using a data-enabled syringe collection container is provided. The method may include providing a data-enabled syringe collection container; monitoring the data-enabled syringe collection container for pre-defined valid dose event criteria; determining whether the data-enabled syringe collection container has met the pre-defined criteria for the valid dose event; and recording the valid dose event upon determining the pre-defined criteria for the valid dose event is met. The data-enabled syringe collection container, may include an upper inlet body; a container body coupled to the upper inlet body; an electronics module configured for sensing and tracking dose events, the electronics module coupled to at least one of the upper inlet body or the container body; and wherein the upper inlet body may include an inlet lid; a first opening; an entry channel; and a receiving assembly including a dropout door, and wherein the inlet lid may be configured for covering and accessing the first opening, the entry channel may be configured to provide a passage way from the first opening to the receiving assembly, and the dropout door may be configured to allow passage through a second opening into the container body. Determining whether the data-enabled syringe collection container has met the pre-defined criteria for the valid dose event may include any one or more of determining if the inlet lid and dropout door are both in an opened state substantially at the same time, determining whether a duration of time the dropout door is open meets a defined time criteria, determining whether the degree of openness of the dropout door has met a defined criteria, and determining whether an amount of time between successive openings of the dropout door meets a defined minimum time criteria. The method may further include detecting, tracking, and communicating data regarding valid dose events and/or dose exception events. Monitoring the data-enabled syringe collection container for pre-defined valid dose event criteria may include, the electronics module continuously monitoring a state of one or more of one or more switches and one or more sensors, and time of a real-time clock in relation to a patient's defined dosing regimen. The method may further include detecting, tracking, and communicating data regarding a patient's actual dose information.

In still yet another embodiment, a method of using a data-enabled syringe collection container for reminding at dose time, then tracking and communicating valid dose events and/or dose exception events is provided. The method may include preparing the data-enabled syringe collection container for use; monitoring valid dose event criteria and medication adherence; determining whether a valid dose event has occurred; and recording actual dose event data. The data-enabled syringe collection container may include an upper inlet body; a container body coupled to the upper inlet body; an electronics module configured for sensing and tracking dose events, the electronics module coupled to at least one of the upper inlet body or the container body; and wherein the upper inlet body may include an inlet lid; a first opening; an entry channel; and a receiving assembly including a dropout door, and wherein the inlet lid may be configured for covering and accessing the first opening, the entry channel may be configured to provide a passage way from the first opening to the receiving assembly, and the dropout door may be configured to allow passage through a second opening into the container body. Preparing the data-enabled syringe collection container for use may include one or more of programming a patient's dosing regimen into a processor of the data-enabled syringe collection container; and setting or resetting a real-time clock of the data-enabled syringe collection container. Preparing the data-enabled syringe collection container for use may further include one or more of loading any updates into the processor of the data-enabled syringe collection container; retrieving any stored dose event data; checking diagnostics of the data-enabled syringe collection container; and labeling the data-enabled syringe collection container. Monitoring valid dose event criteria and medication adherence may include a processor of the data-enabled syringe collection container receiving and interpreting data from one or more of the patient's dosing regimen; a dose detection algorithm; the real-time clock; whether and when valid dose events occur and whether they are in compliance with/adherent to dosing instructions stored in the patient's dosing regimen. The electronics module may include one or more indicators capable of being monitored by the patient. The one or more indicators may be one or more of visual and audible. The one or more indicators may be configured to indicate to the patient any one or more of, time to take a dose, a dose has been missed, and time for a prescription refill. The method may further include transmitting data from the data-enabled syringe collection container to an external computing device using a communications interface. The method may further include following an actual dose event, deactivating any previously activated indicators and activating an applicable indicator according to the patient's dosing regimen and recording the actual dose event data. Data from the data-enabled syringe collection container may be transmitted to one or more of a patient, a caretaker, and/or an authorized party via the communications interface. If the recorded actual dose event is a missed dose event according to a patient's dosing regimen the one or more indicators indicate a missed dose, and if the recorded actual dose event is a valid dose event according to the patient's dosing regimen the one or more indicators indicate a taken dose, and the applicable actual dose event is recorded. The method may further include determining whether a prescription refill is needed based on a number of valid dose events as compared to the recorded actual dose data and a patient's dosing regimen. If it is determined a prescription refill is needed the one or more indicators may indicate a prescription refill is needed. A prescription refill notice may be sent to one or more of a patient, a pharmacy, and any other caretaker or authorized party via a communications interface.

BRIEF DESCRIPTION OF THE DRAWINGS

Figure 1:
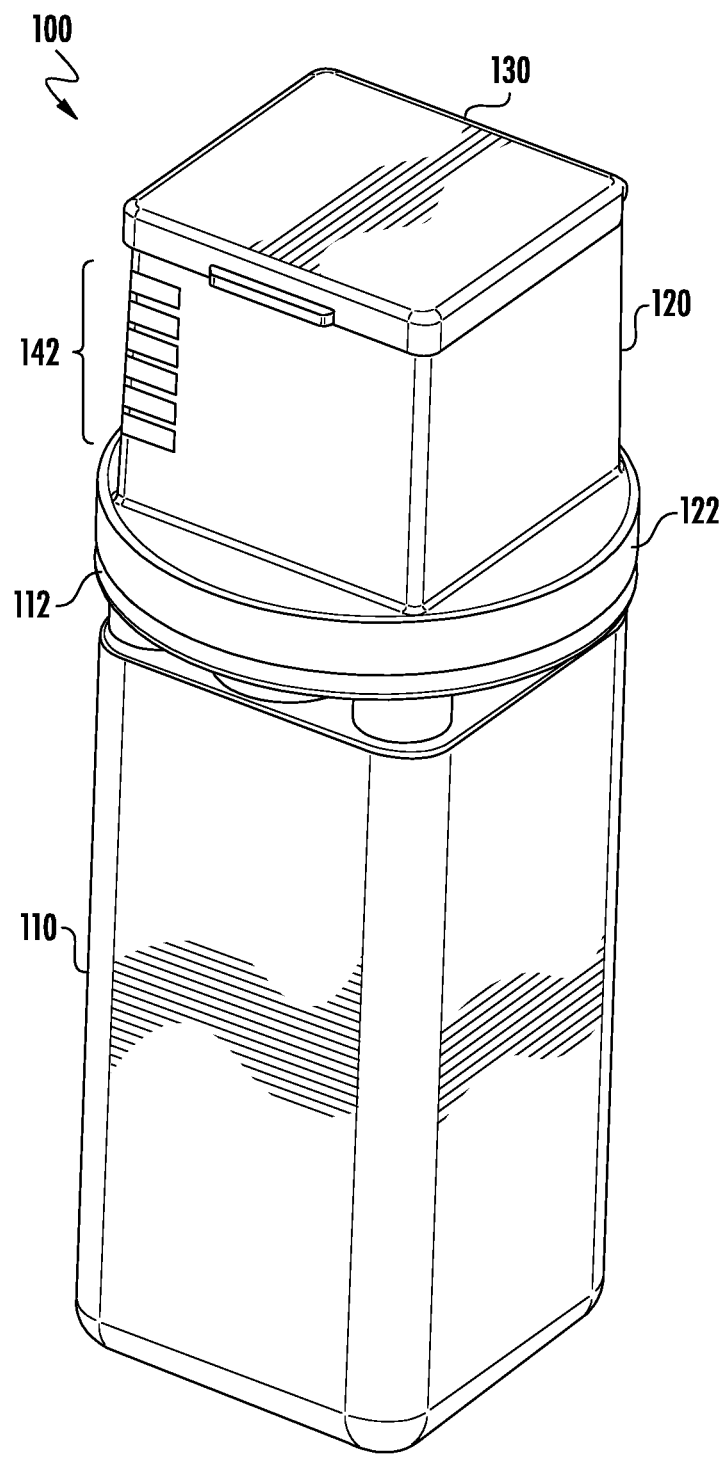
Figure 2:
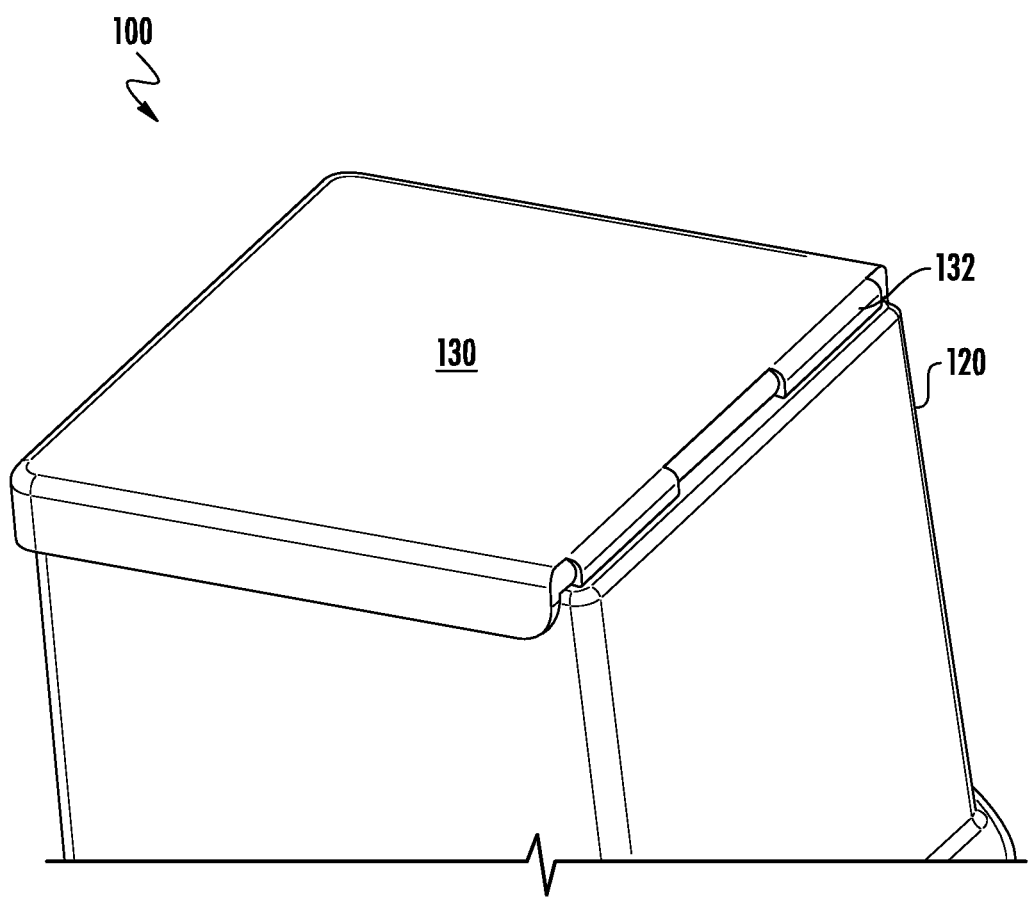
Figure 3:
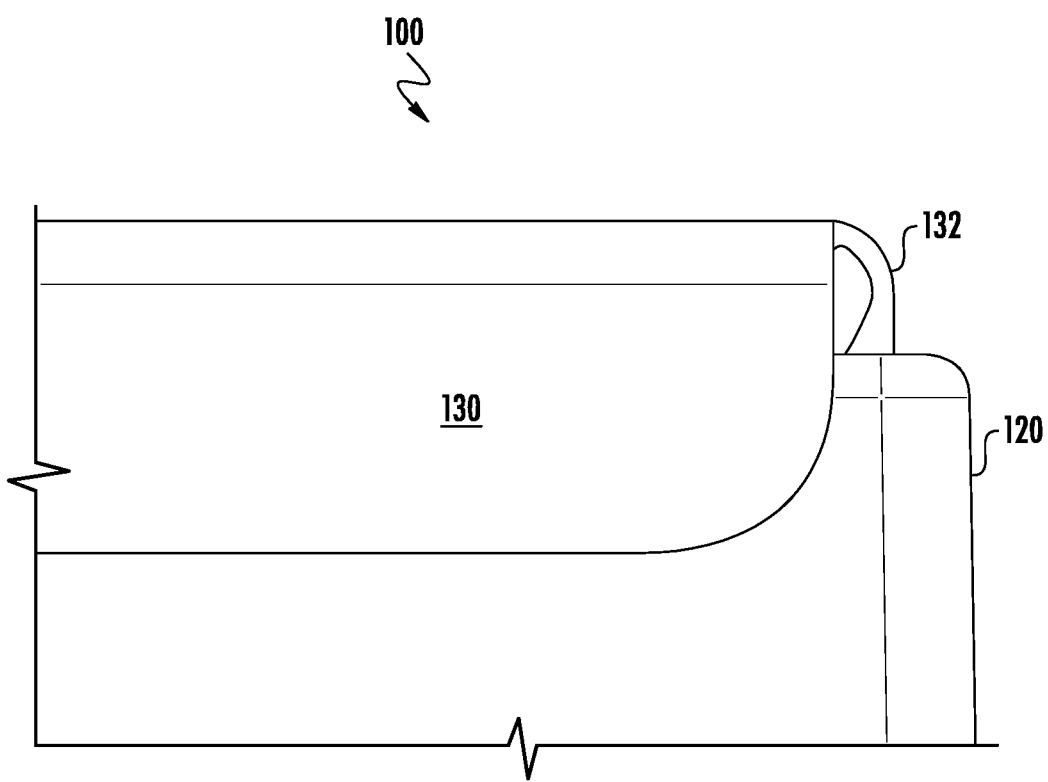
Figure 4:
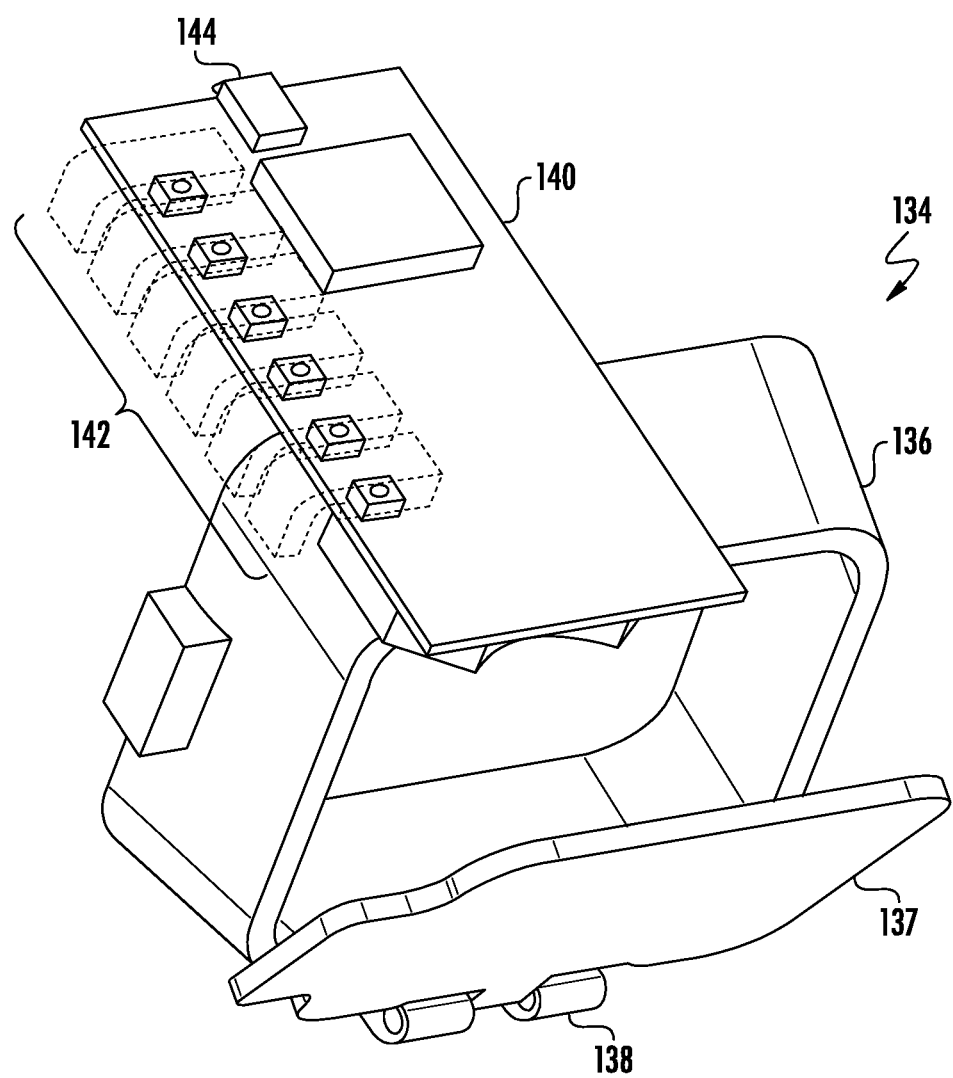
Figure 5:
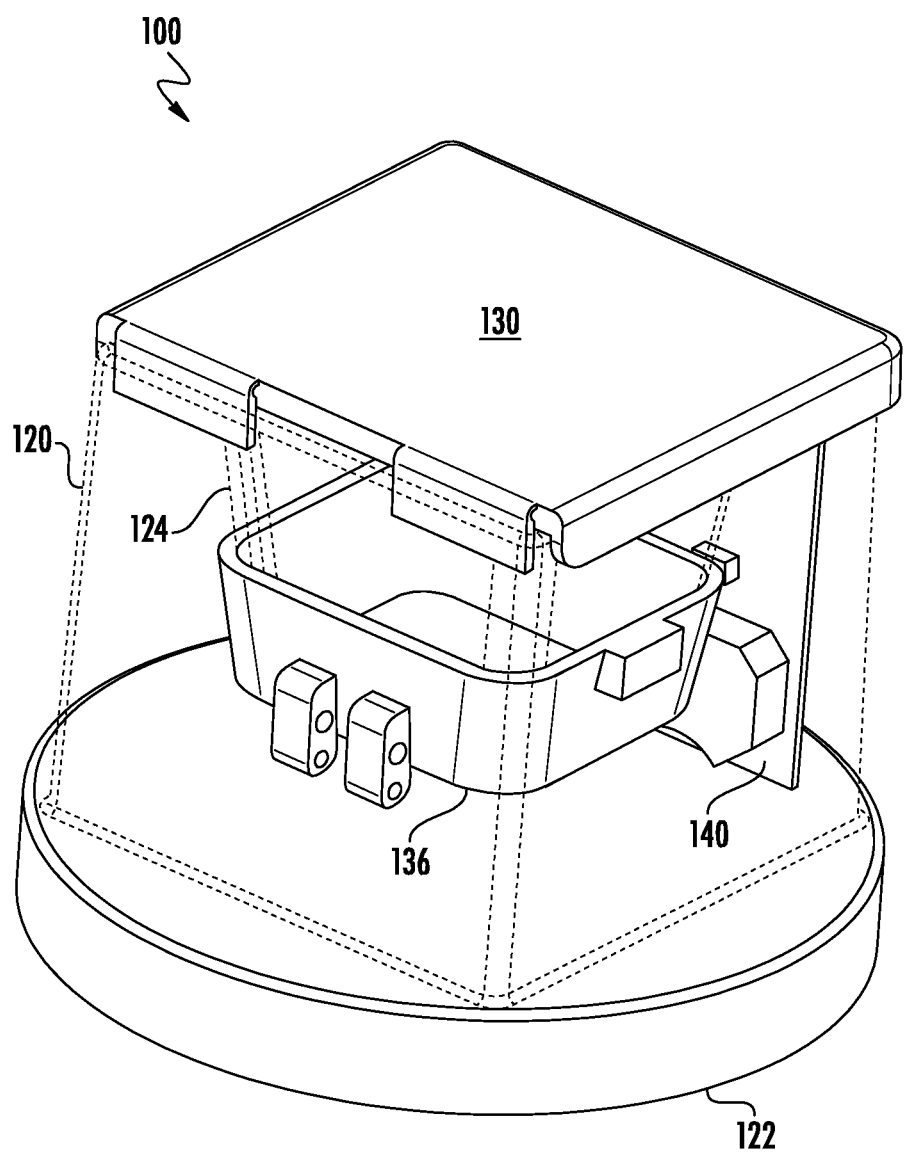
Figure 6:
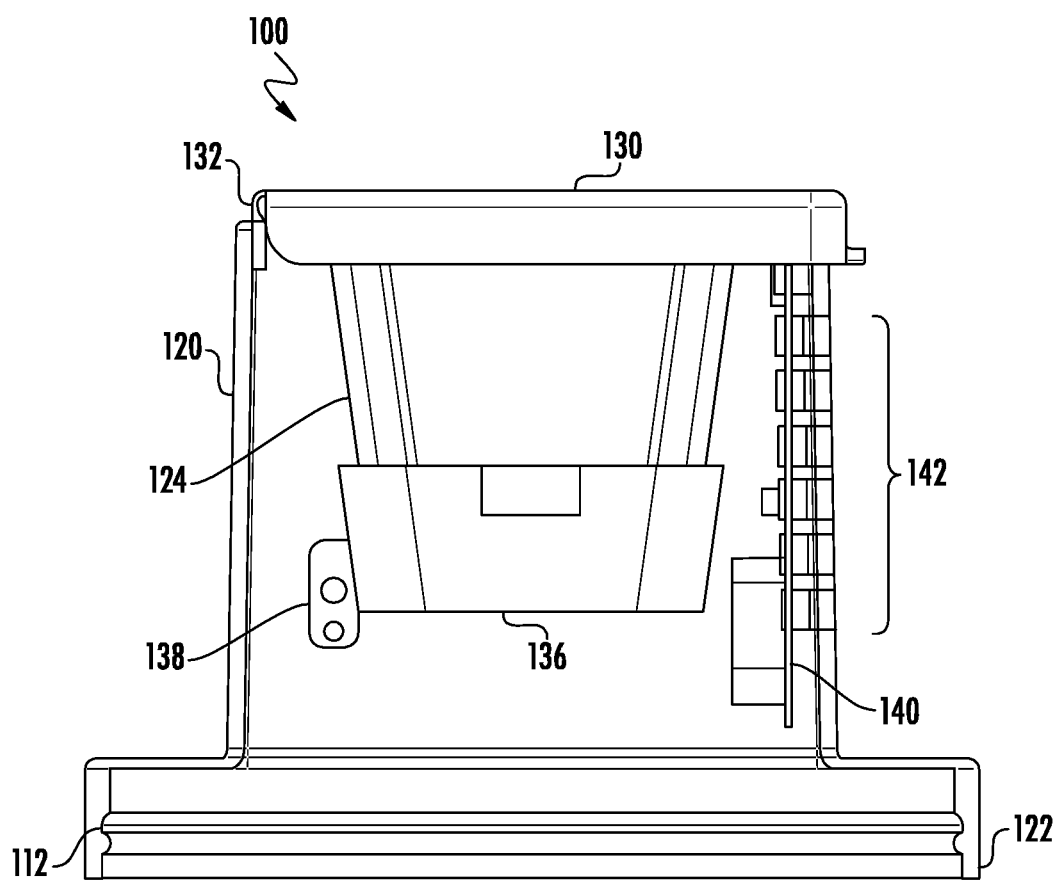
Figure 7:
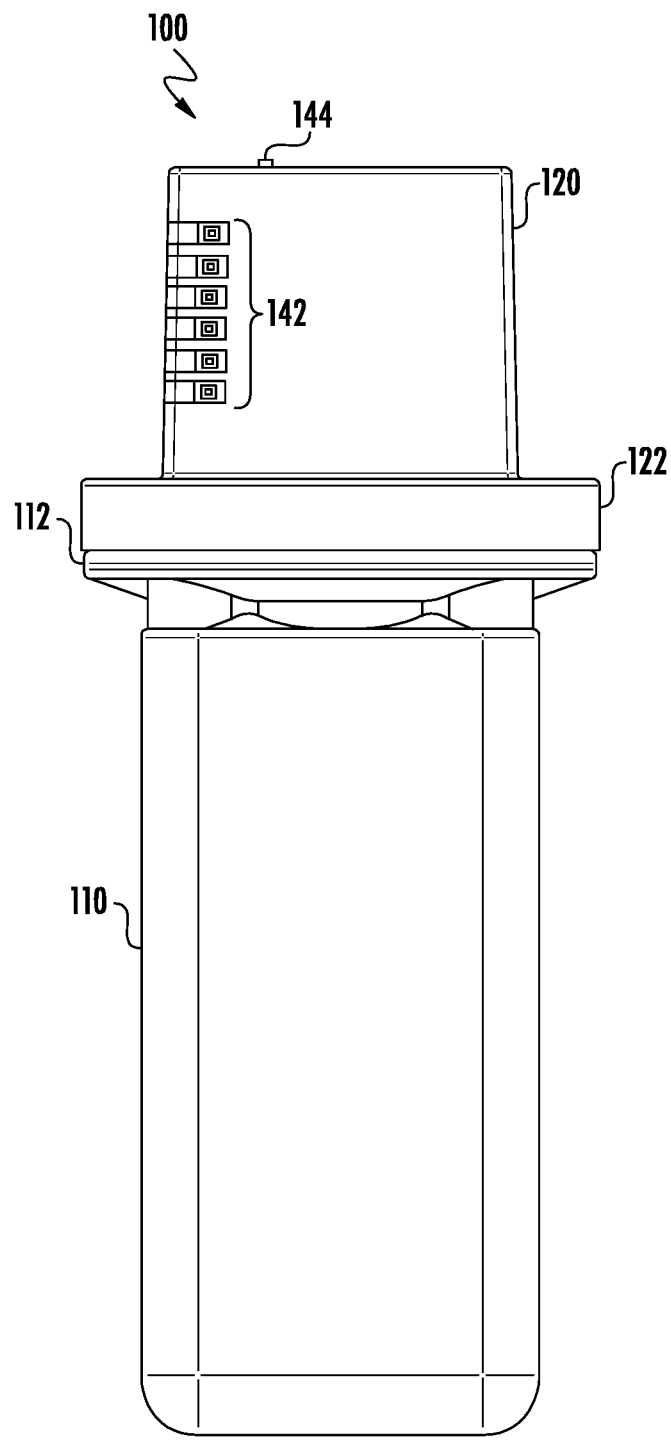
Figure 8:
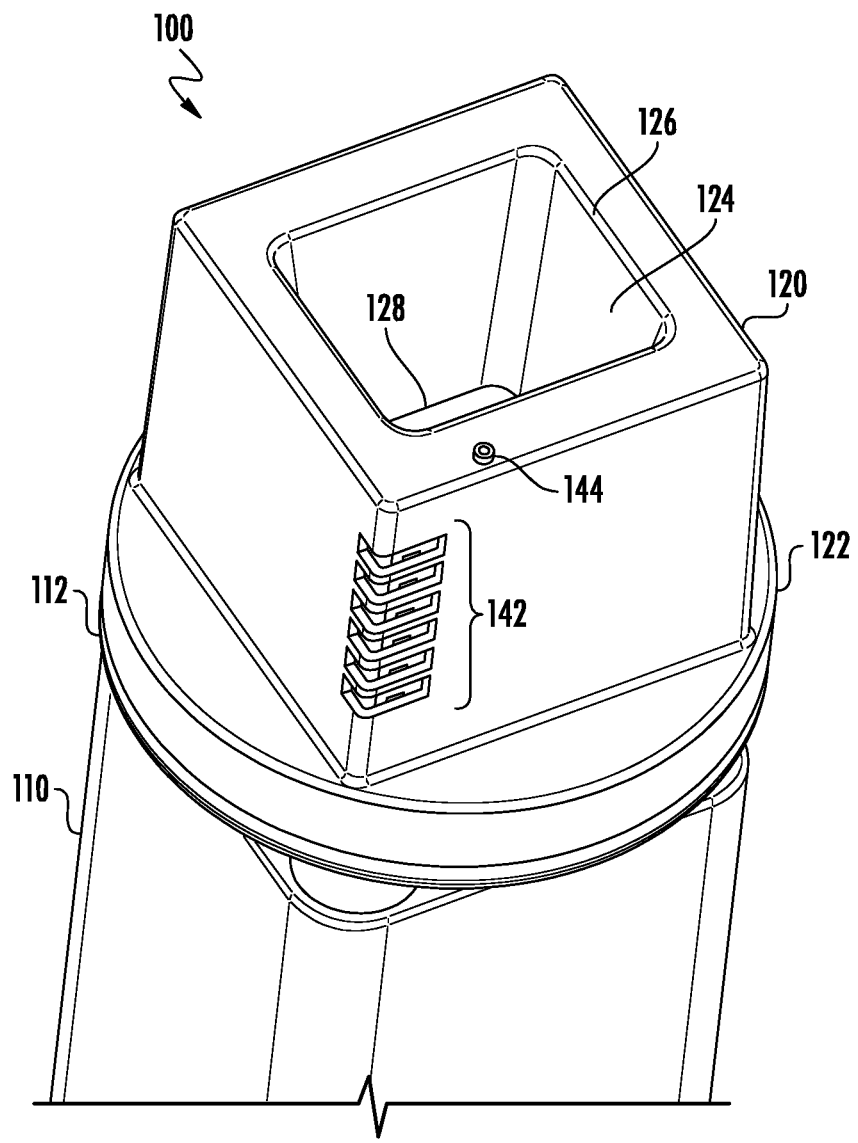
Figure 9:
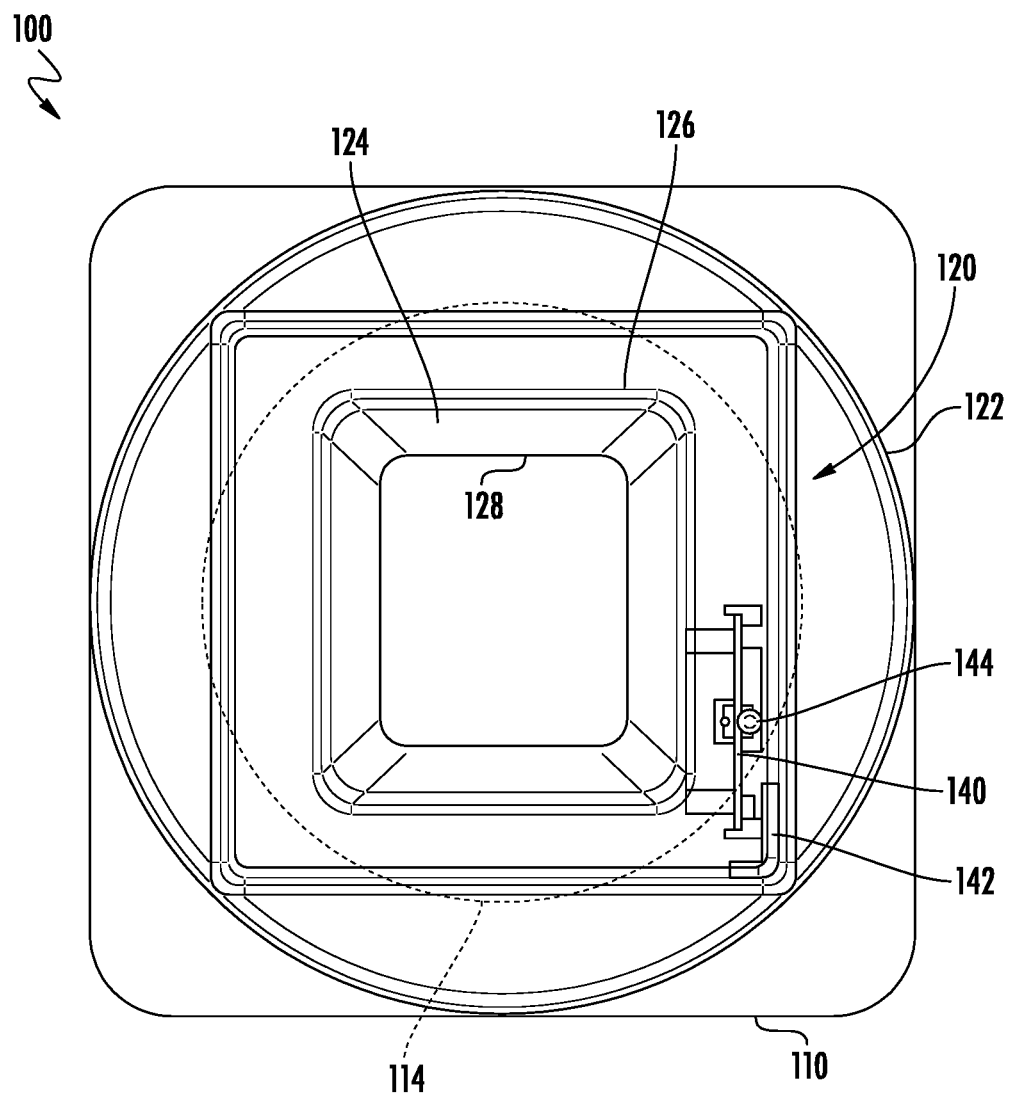
Figure 10:
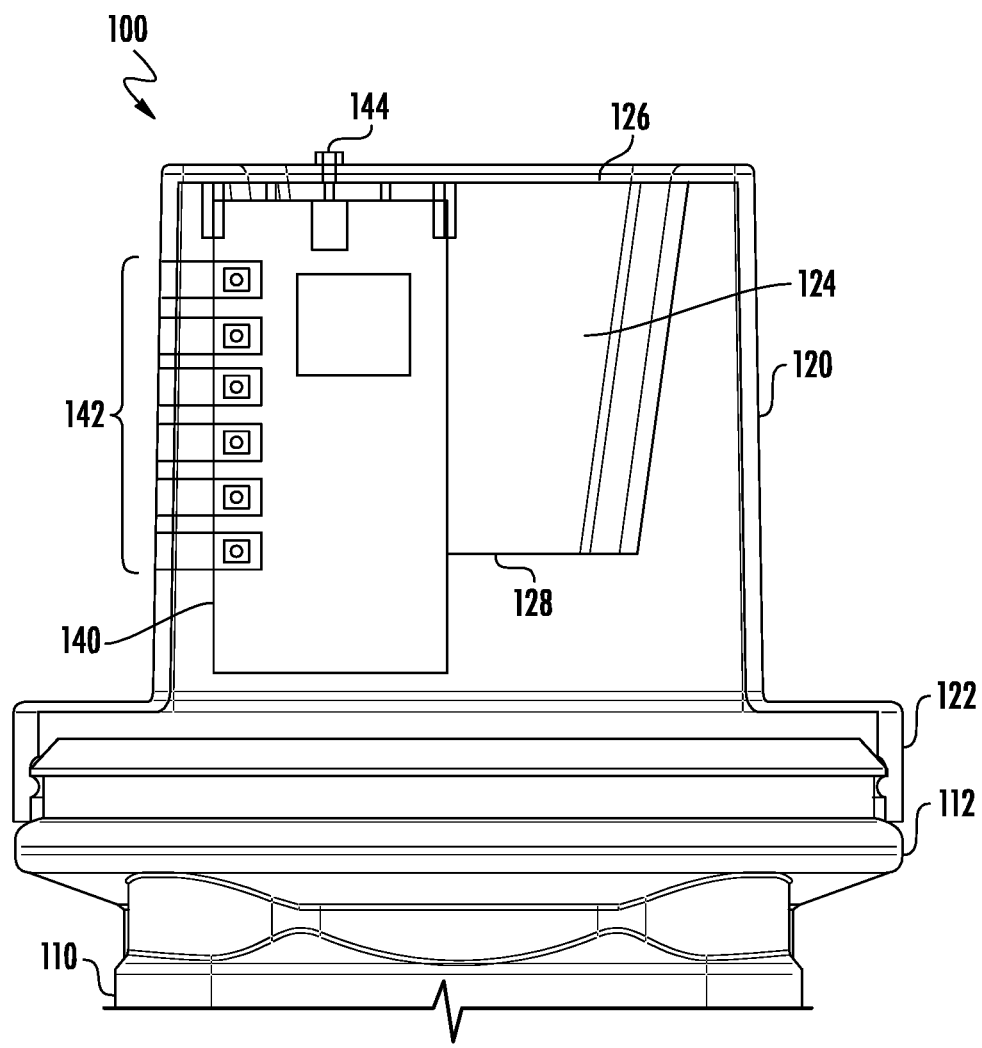
Figure 11:
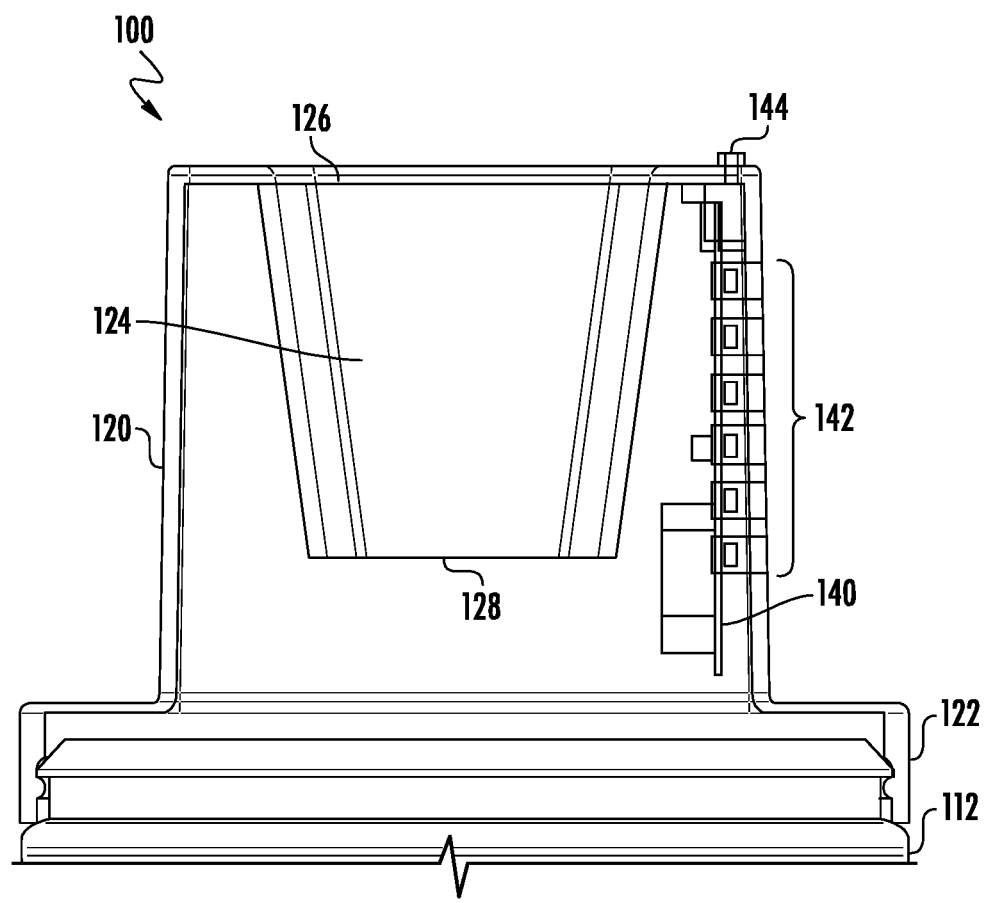
Figure 12:
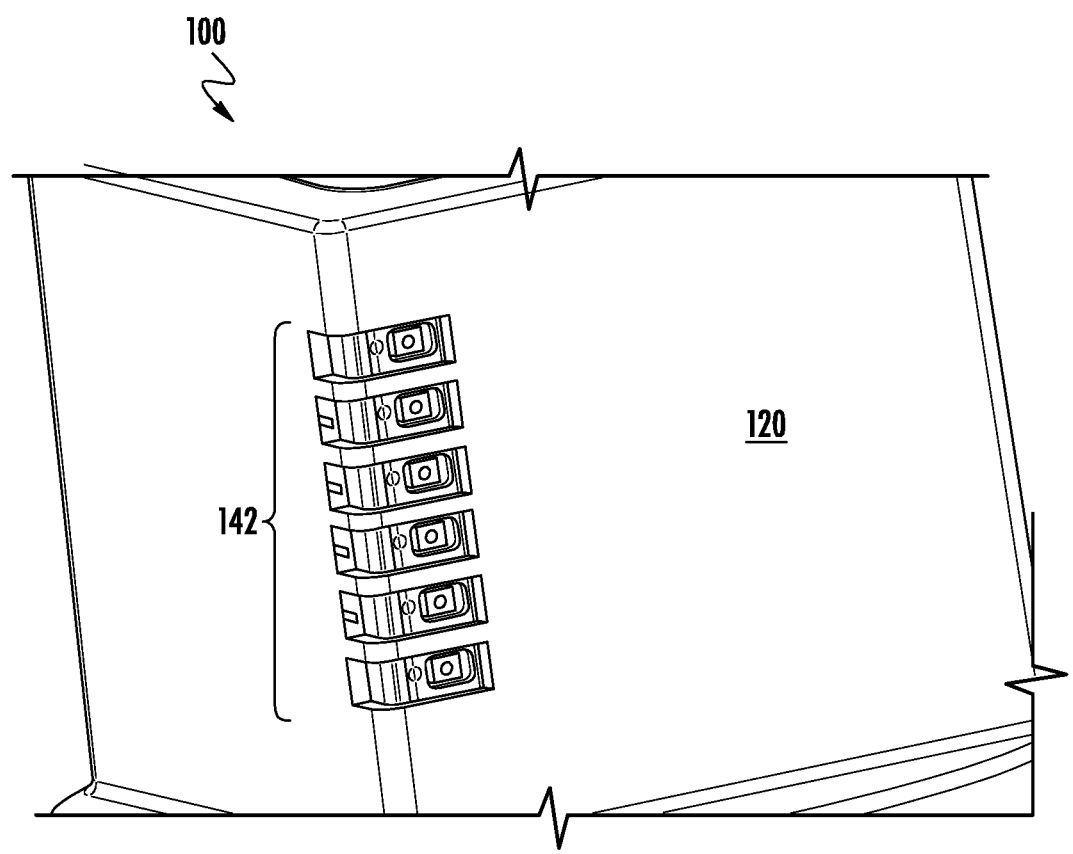
Figure 13:
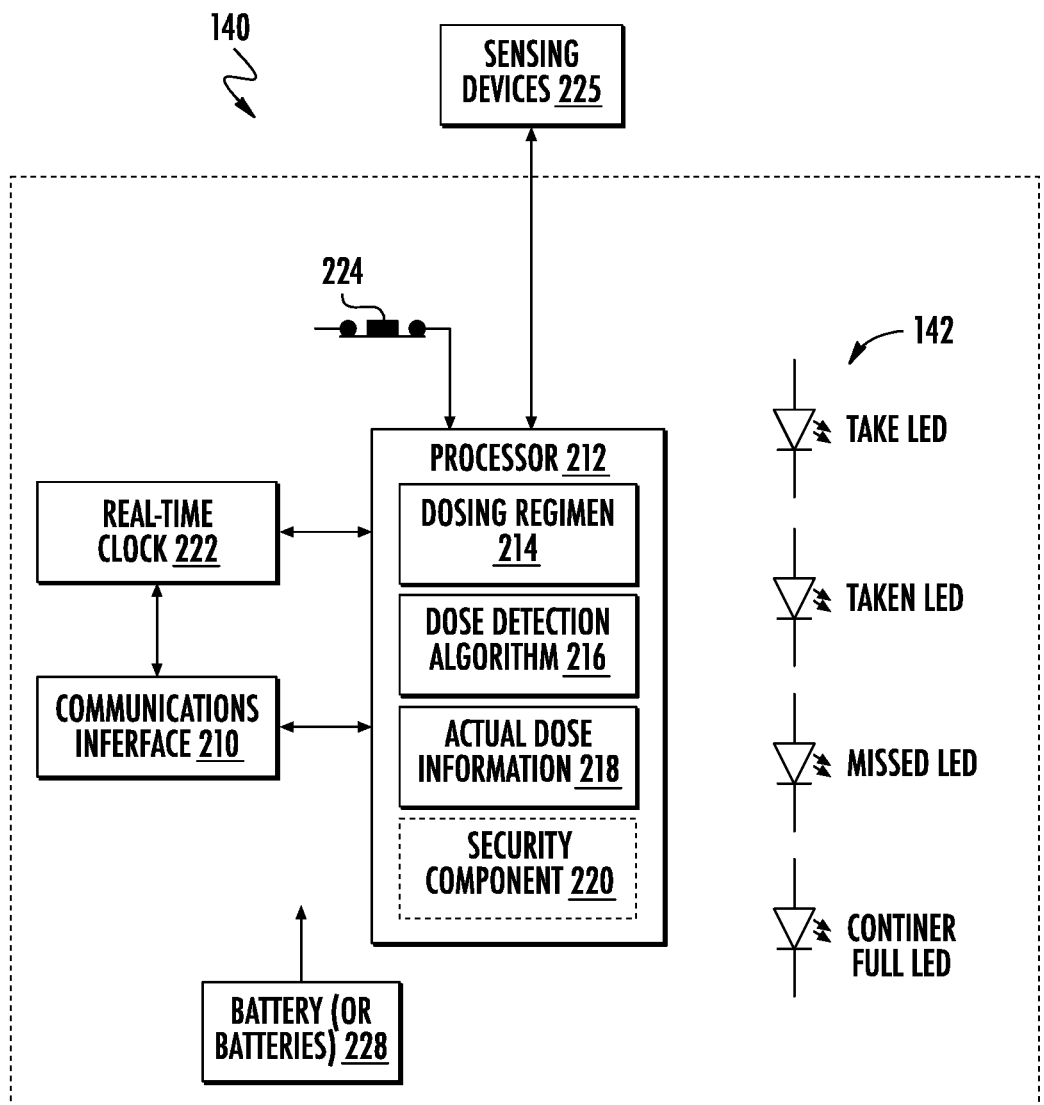
Figure 14A:
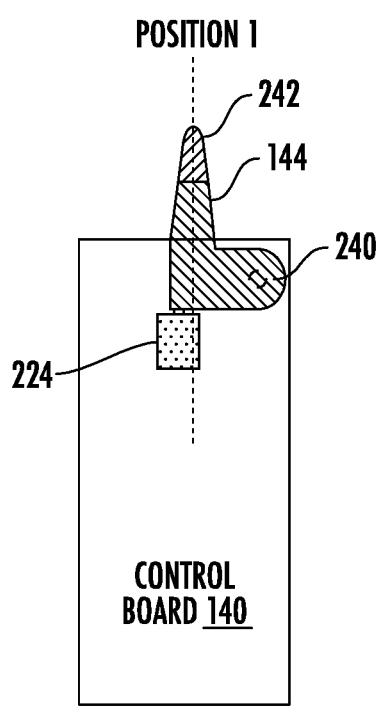
Figure 14B:
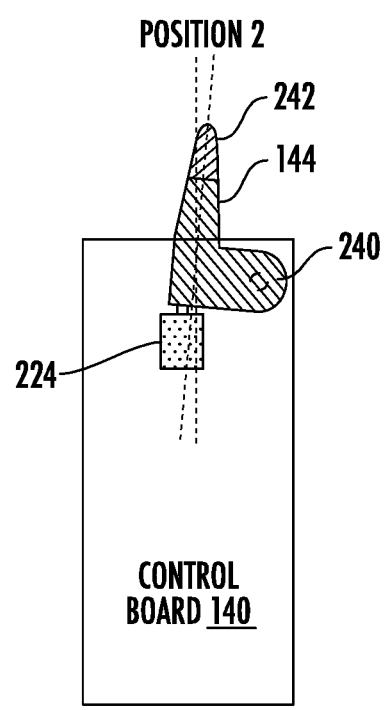
Figure 15:
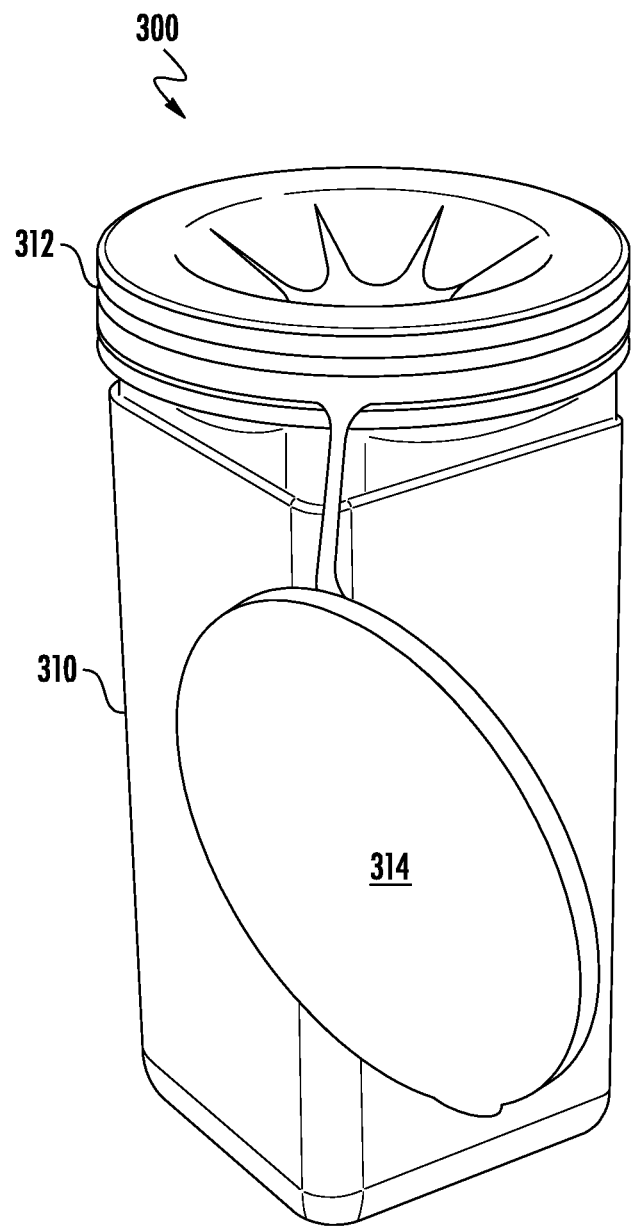
Figure 16:
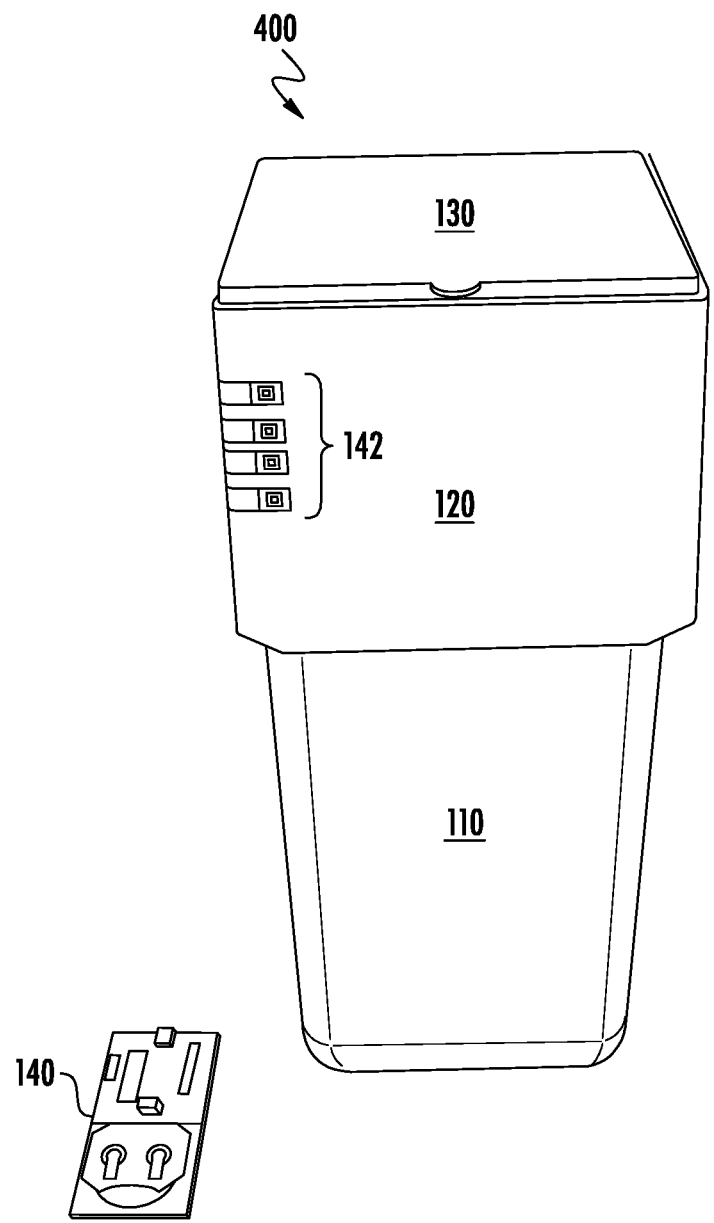
Figure 17:
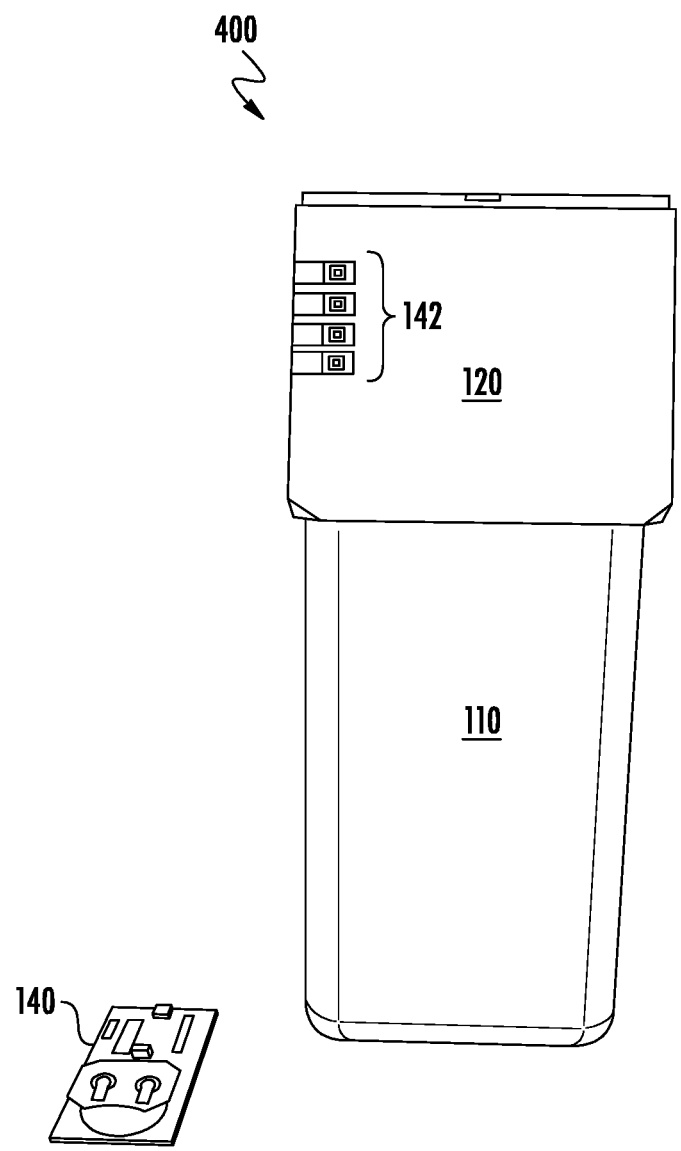
Figure 18:
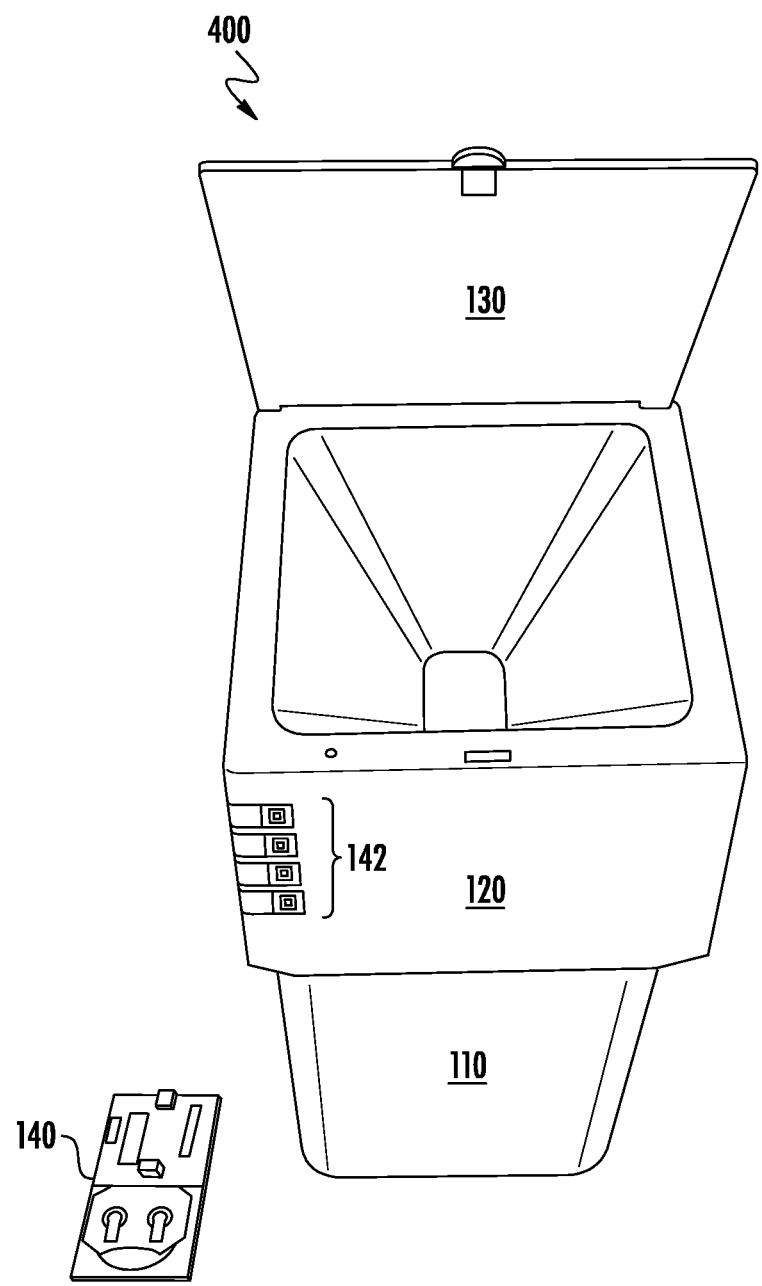
Figure 21:
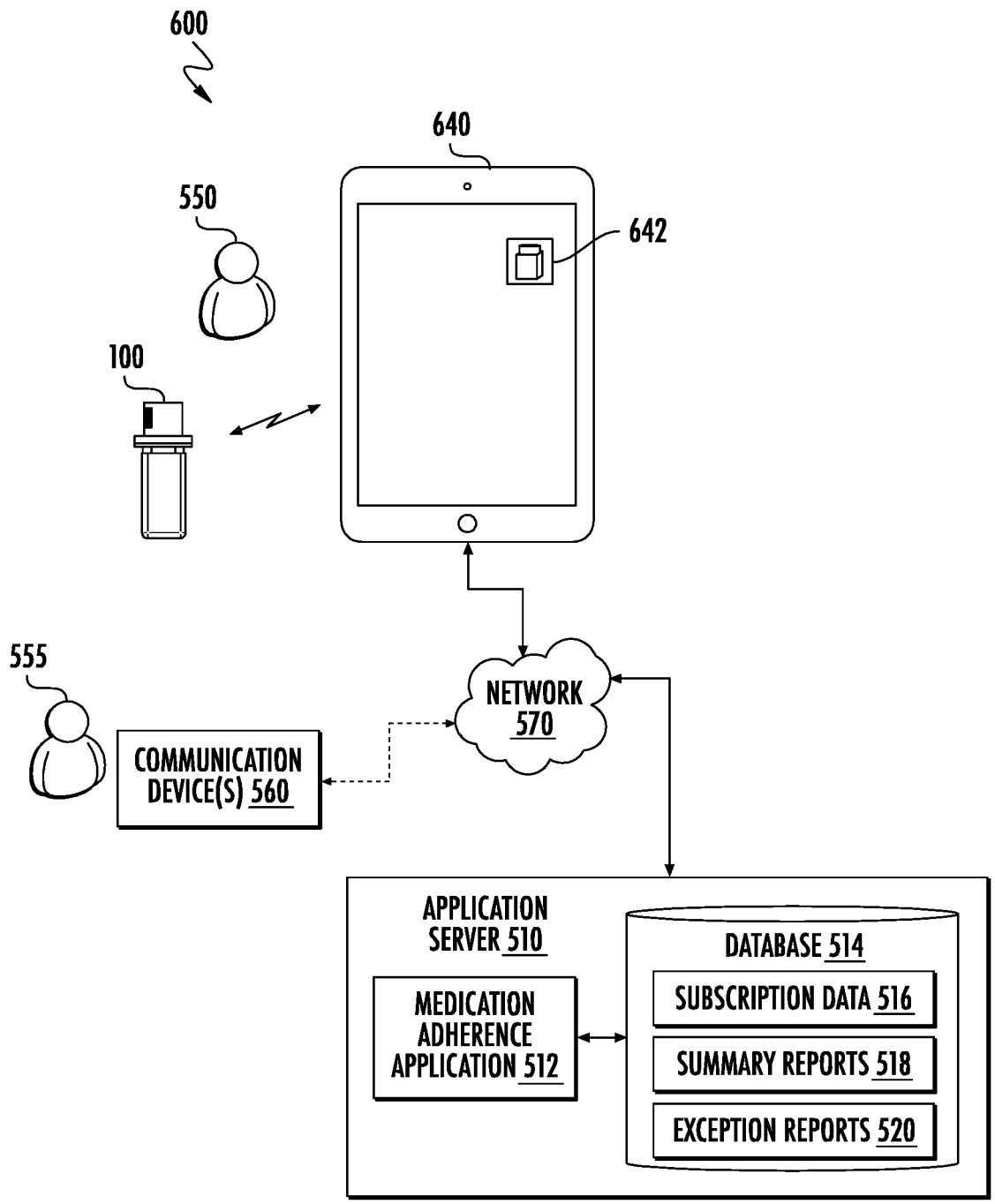
Figure 22:
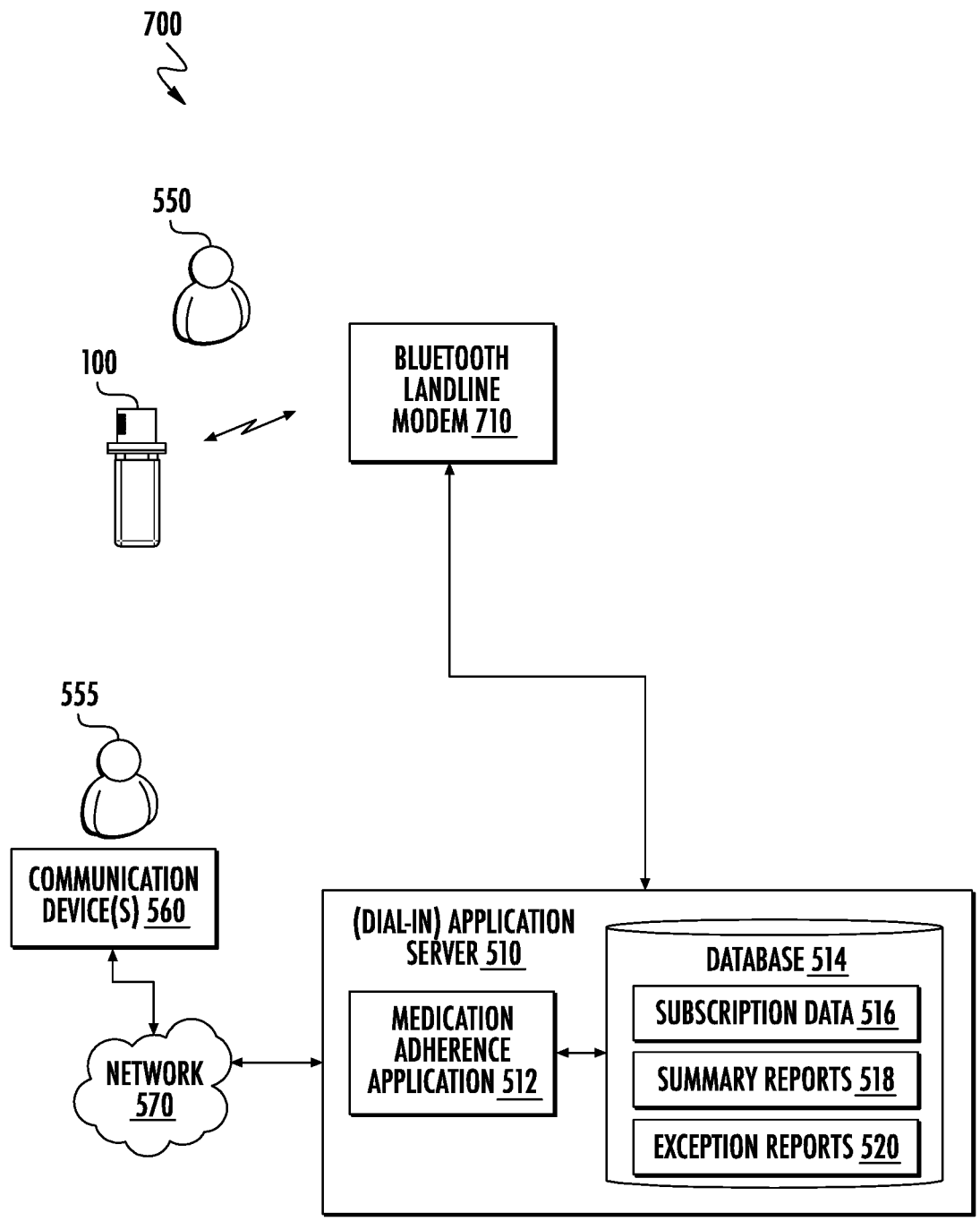
Figure 23:
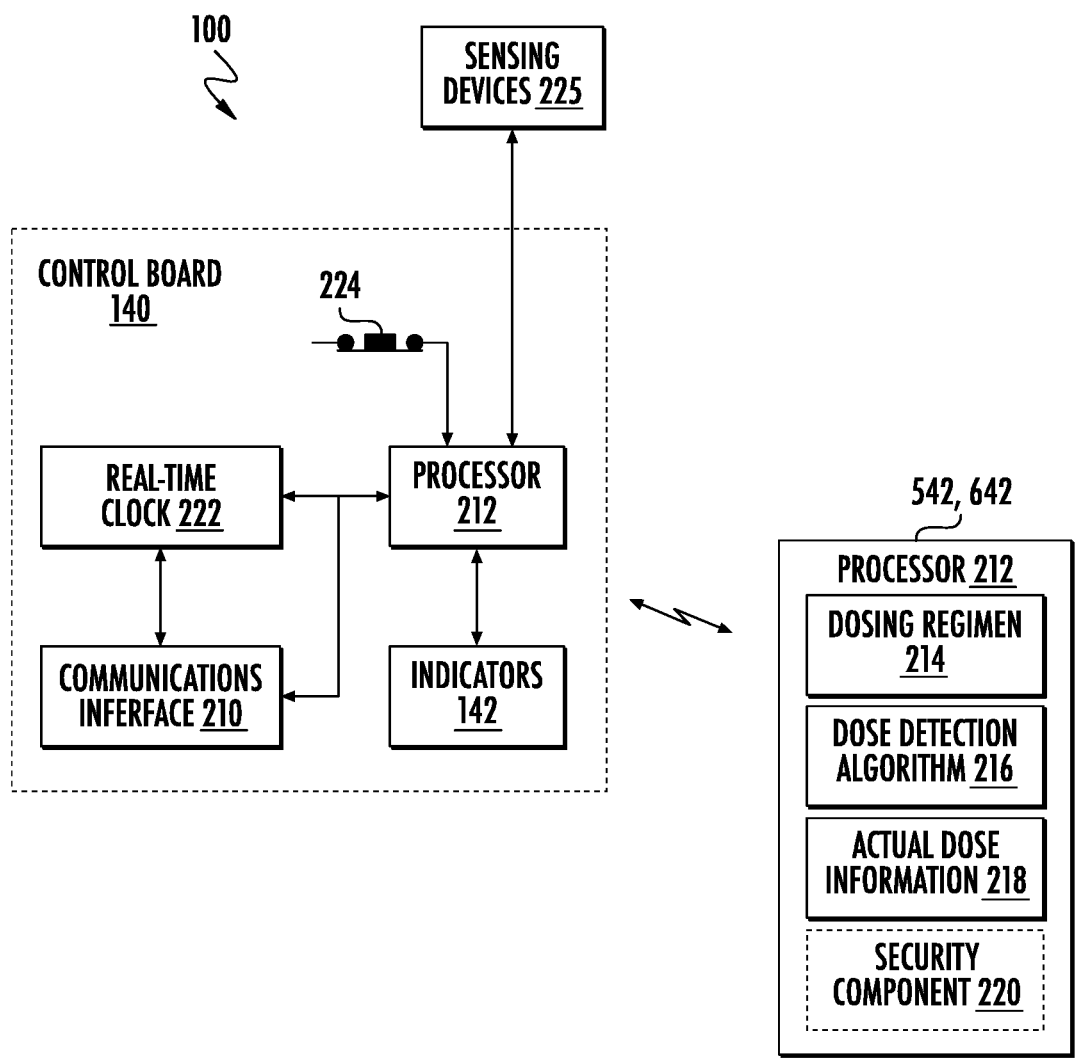

Having thus described the presently disclosed subject matter in general terms, reference will now be made to the accompanying Drawings, which are not necessarily drawn to scale, and wherein:

FIG. 1 illustrates a perspective view of an example of the presently disclosed data-enabled syringe collection container for monitoring a patient's medication adherence with respect to self-inject medications and facilitating dose-reminder and/or dose-taken notifications;

FIG. 2 illustrates a perspective view of a portion of a data-enabled fitting of the presently disclosed data-enabled syringe collection container;

FIG. 3 illustrates a side view of a hinge-portion of the data-enabled fitting of the presently disclosed data-enabled syringe collection container;

FIG. 4 illustrates a perspective view of a trapdoor assembly and a control board of the presently disclosed data-enabled syringe collection container;

FIG. 5 and FIG. 6 illustrate a transparent perspective view and a transparent side view, respectively, of the data-enabled fitting of the presently disclosed data-enabled syringe collection container;

FIG. 7 and FIG. 8 illustrate a side view and a perspective view, respectively, of an example of the presently disclosed data-enabled syringe collection container and absent the container lid and trapdoor assembly;

FIG. 9, FIG. 10, and FIG. 11 illustrate a top transparent view, a front transparent view, and a side transparent view, respectively, of an example of the data-enabled fitting of the presently disclosed data-enabled syringe collection container and absent the container lid and trapdoor assembly;

FIG. 12 illustrates a perspective view of a portion of the data-enabled fitting of the presently disclosed data-enabled syringe collection container and absent the container lid;

FIG. 13 illustrates a block diagram of an example of the control board of the presently disclosed data-enabled syringe collection container;

FIG. 14A and FIG. 14B illustrate plan views of an example of an actuation lever in relation to the control board of the presently disclosed data-enabled syringe collection container shown in FIG. 7, FIG. 8, and FIG. 9;

FIG. 15 illustrates a perspective view of an example of a conventional syringe collection container that is not data-enabled;

FIG. 16, FIG. 17, and FIG. 18 show photos of another example of the presently disclosed data-enabled syringe collection container;

FIG. 19, FIG. 20, FIG. 21, and FIG. 22 illustrate block diagrams of examples of medication adherence systems that include the presently disclosed data-enabled syringe collection containers; and FIG. 23 illustrates a block diagram of another configuration of the control board of the presently disclosed data-enabled syringe collection container, wherein the configuration supports remote processing capability.

DETAILED DESCRIPTION

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

The presently disclosed subject matter provides a data-enabled syringe collection container and systems using same for monitoring a patient's medication adherence with respect to self-inject medications and facilitating dose-reminder as well as dose-taken and related notifications. Namely, the presently disclosed subject matter provides an electronics module integrated into the fitting of a syringe collection container, thereby forming a data-enabled fitting that can be affixed to the container body that holds, for example, spent syringes and/or any other related items of the data-enabled syringe collection container. A tapered entry channel is provided in the data-enabled fitting through which, for example, a spent syringe may pass. Mechanisms of the data-enabled fitting are used to detect and log the date and time of any syringe passing through the entry channel and into the container body. In this way, the data-enabled fitting of the data-enabled syringe collection container can be used to detect and log syringe disposal events, wherein a syringe disposal event indicates or correlates to an injection dose event.

The electronics module of the data-enabled syringe collection container includes circuitry for reminding at dose time, then detecting valid dose events, as well as for processing and communicating information about valid dose events and/or dose-exception events, such as missed doses. In one example, using a dose detection algorithm, a dose event is deemed valid based on sensing that both the container lid and a trapdoor at the lower portion of the entry channel are open at substantially the same time. In another example, a dose event is deemed valid based on (1) sensing that both the container lid and the trapdoor are open at substantially the same time, and (2) sensing that the amount of time that the trapdoor is open corresponds to an expected amount of time that it takes for a spent syringe to pass through the trapdoor. Other qualifying parameters for determining dose events and/or dose exception events may include, but are not limited to, the amount of time that the trapdoor is open, the physical amount that the trapdoor is open (i.e., degree of openness), and multiple trapdoor open events occurring close together in time. Examples of dose exception events may include, but are not limited to, missed doses, extra doses, early doses, and late doses.

In some embodiments, the data-enabled syringe collection container records digital information about dose events and/or dose-exception events (e.g., missed, extra, early, and late doses) that are automatically generated and stored thereon, wherein the digital information can be used to determine periodically or continuously whether the prescribed dosing regimen is being followed. This enables interventions as necessary in real time, such as a phone call, text, or email, from a clinician or caregiver to the patient reminding the patient that it's now dose time.

Further, medication adherence systems are provided that include the data-enabled syringe collection containers, wherein the medication adherence systems can be used for monitoring a patient's medication adherence and facilitating dose-reminder and/or dose-taken notifications. Namely, the medication adherence systems can be used for processing information from the data-enabled syringe collection containers, wherein the data-enabled syringe collection containers provide mechanisms for reminding at dose time, then tracking and communicating valid dose events, as well as missed, extra, early, and/or late dose events. Other uses include messages such as "Wait for 'Take now' signal," "Check blood pressure," "Set Dr. appointment," and the like.

The medication adherence systems include a centralized server, such as a cloud server, for collecting and processing the patient-specific information from the data-enabled syringe collection containers. Namely, the data-enabled syringe collection container records digital information about dose events and/or dose-exception events (e.g., missed, extra, early, and late doses) that are automatically generated and stored thereon. Accordingly, the centralized server is used to analyze the information from the patient's data-enabled syringe collection container, wherein the digital information can be used to determine periodically or continuously whether the prescribed dosing regimen is being followed. Stakeholders, such as clinicians and caregivers, may be notified in real time when it is necessary to intervene, owing to missed doses or other non-adherence, In some embodiments, the patient's data-enabled syringe collection container can transmit information wirelessly to, for example, the patient's mobile phone or computing device. Then, the patient's mobile phone or computing device is used to transmit the patient-specific information to the centralized server.

FIG. 1 illustrates a perspective view of an example of the presently disclosed data-enabled syringe collection container 100 for monitoring a patient's medication adherence with respect to self-inject medications and facilitating dose-reminder and/or dose-taken notifications. Namely, the data-enabled syringe collection container 100 includes mechanisms for detecting and logging date and time of syringe disposal events wherein a syringe disposal event indicates or correlates to an injection dose event. Further, with respect to facilitating dose-reminder and/or dose-taken notifications, the data-enabled syringe collection container 100 can be used for reminding at dose time, then tracking and communicating valid dose events, as well as missed, extra, early, and/or late dose events, and related events and messages such as "Wait for 'Take now' signal," "Check blood pressure," "Set Dr. appointment," and the like.

The data-enabled syringe collection container 100 includes a container body 110 that has a container upper rim 112 around the opening of container body 110. Further, the outside of the container upper rim 112 of the container body 110 is threaded. In this example, the cross-sectional footprint of the container body 110 is substantially square and the cross-sectional footprint of the container upper rim 112 is substantially circular. However, this is exemplary only. In another example, the cross-sectional footprint of both the container body 110 and the container upper rim 112 is substantially circular.

The data-enabled syringe collection container 100 further includes a data-enabled fitting 120 through which a spent syringe passes on its way to disposal into the container body 110. The data-enabled fitting 120 includes a fitting lower rim 122. Further, the inside of the fitting lower rim 122 of the data-enabled fitting 120 is threaded. In this example, the cross-sectional footprint of the main body of the data-enabled fitting 120 is substantially square and the cross-sectional footprint of the fitting lower rim 122 is substantially circular. However, this is exemplary only. In another example, the cross-sectional footprint of both the main body of the data-enabled fitting 120 and the fitting lower rim 122 is substantially circular.

Because the inside of the fitting lower rim 122 of the data-enabled fitting 120 is threaded and the outside of the container upper rim 112 of the container body 110 is threaded, the data-enabled fitting 120 can be fastened to the container body 110 by screwing. In this way, the data-enabled fitting 120 can be mechanically coupled to the container body 110 (see FIG. 6). Additionally, the data-enabled fitting 120 includes a container lid 130 that is hingeably coupled to the top of the data-enabled fitting 120 via a lid hinge 132. Referring now to FIG. 2 is a perspective view of the lid-portion of the data-enabled fitting 120. Further, FIG. 3 shows a close-up side view of the lid hinge 132 of the data-enabled fitting 120.

Referring now to FIG. 4, FIG. 5, and FIG. 6 for more details of the presently disclosed data-enabled syringe collection container 100, FIG. 4 shows a perspective view of a trapdoor assembly 134 and a control board 140 of the data-enabled syringe collection container 100 while FIG. 5 and FIG. 6 show a transparent perspective view and a transparent side view, respectively, of the data-enabled fitting 120 of the data-enabled syringe collection container 100.

The data-enabled fitting 120 includes an entry channel 124, which is a passageway through which a spent syringe (not shown) may pass through the data-enabled fitting 120 on its way to disposal into the container body 110. The entry channel 124 is tapered; namely, the upper opening of the entry channel 124 is larger than the lower opening of the entry channel 124 (see FIG. 8, FIG. 9, FIG. 10, FIG. 11). The trapdoor assembly 134 is designed to be installed at the lower opening of the entry channel 124. For example, the trapdoor assembly 134 includes a trapdoor frame 136 and a trapdoor 137, wherein the trapdoor 137 is hingeably coupled to the trapdoor frame 136 via a trapdoor hinge 138. The trapdoor 137 is a one way trapdoor. Namely, the design of the trapdoor assembly 134 is such that the trapdoor 137 can open downward only and into the container body 110. Additionally, the trapdoor hinge 138 is spring-loaded (not shown) so that the trapdoor 137 will automatically close after an article has passed through. Further, FIG. 6 shows that the trapdoor hinge 138 of the trapdoor assembly 134 and the lid hinge 132 of the container lid 130 are oriented on the same side of the data-enabled fitting 120.

The container body 110, the data-enabled fitting 120, the container lid 130, and the components of the trapdoor assembly 134 may be formed of any suitably rigid and lightweight material, such as molded high-density polyethylene (HDPE), i.e., molded plastic. In one example, the data-enabled syringe collection container 100 has an overall height of about 10 inches. Further, the container body 110 can be, for example, about 4.5 inches square. Further, the main body of the data-enabled fitting 120 can be, for example, about 3.5 inches square. Further, the container body 110 can have a volume of, for example, about 1.4 quarts. In another example, the container body 110 can be sized to hold a certain number or volume of spent syringes, such as one month's worth of spent syringes based on the patient's prescribed dosing regimen.

The control board 140 can be, for example, a printed circuit board (PCB) for implementing any control electronics (see FIG. 13) needed for the operation of the data-enabled syringe collection container 100. A set of indicators 142 are provided on the control board 140. Further, the control board 140 includes an actuation lever 144. The tip of the actuation lever 144 engages with the container lid 130 for indicating whether the container lid 130 is open or closed. More details of the actuation lever 144 are shown and described hereinbelow with reference to FIG. 14A and FIG. 14B.

In one example, the control board 140 is installed on the side of the data-enabled fitting 120 that is opposite the trapdoor hinge 138 of the trapdoor assembly 134. Further, the long dimension of the control board 140 is oriented vertically and with the actuation lever 144 at the top. In one example, the set of indicators 142 includes six light-emitting diodes (LEDs) of any color and arrangement. However, this is exemplary only. The control board 140 can include any number of indicators 142. In this example, a set of corner lenses is provided in one corner of the data-enabled fitting 120, wherein each of the corner lenses aligns with a corresponding LED. Examples of the meaning or purpose of the indicators 142 is described hereinbelow with reference to FIG. 13.

Generally, the control board 140 includes active and passive electrical and/or mechanical components for sensing when the container lid 130 is open and closed, for tracking the duration and time that the container lid 130 is open, for sensing when the trapdoor 137 is open and closed, for tracking the duration and time that the container lid 130 is open, for tracking the duration and time that the trapdoor 137 is open, for determining the physical amount that the trapdoor 137 is open (i.e., degree of openness), for processing these sensing mechanisms with respect to the patient's dosing regimen, and for storing and communicating information, such as about doses taken, doses missed, and/or extra doses, and the like. More details of the control board 140 are shown and described hereinbelow with reference to FIG. 13.

FIG. 7 through FIG. 12 show more details of the presently disclosed data-enabled syringe collection container 100. For example, FIG. 7 and FIG. 8 show a side view and a perspective view, respectively, of an example of the data-enabled syringe collection container 100 and absent the container lid 130 and the trapdoor assembly 134. FIG. 9, FIG. 10, and FIG. 11 show a first transparent side view, a second transparent side view, and a transparent perspective view, respectively, of the data-enabled fitting 120 absent the container lid 130 and the trapdoor assembly 134. FIG. 12 shows a perspective view of a portion of the data-enabled fitting 120 and absent the container lid 130.

In particular, FIG. 8, FIG. 9, FIG. 10, and FIG. 11 show that the entry channel 124 of the data-enabled fitting 120 has a channel upper opening 126 and a channel lower opening 128, wherein the channel upper opening 126 is larger than the channel lower opening 128 and thereby forming the taper. Further, FIG. 8, FIG. 9, FIG. 10, and FIG. 11 show the tip of the actuation lever 144 protruding through the upper edge of the data-enabled fitting 120 and in relation to the container lid 130 (not shown).

FIG. 13 illustrates a block diagram of an example of the control board 140 of the presently disclosed data-enabled syringe collection container 100 for monitoring a patient's medication adherence with respect to self-inject medications and facilitating dose-reminder and/or dose-taken notifications. Namely, the control board 140 supports mechanisms for detecting and logging syringe disposal events wherein a syringe disposal event indicates or correlates to an injection dose event. Further, with respect to facilitating dose-reminder and/or dose-taken notifications, the control board 140 can be used for processing and communicating information about valid dose events, as well as missed, extra, early, and/or late dose events and related events and messages such as "Wait for 'Take now' signal," "Check blood pressure," "Set Dr. appointment," and the like.

Again, the control board 140 is circuitry that can be implemented as a PCB. In this example, the control board 140 includes a communications interface 210; a processor 212 that further includes the patient's dosing regimen 214, a dose detection algorithm 216, actual dose information 218, and optionally a security component 220; a real-time clock 222; a switch 224 (e.g., a momentary contact switch); and the one or more indicators 142. The components of the control board 140 are powered by one or more batteries 228. Each of the batteries 228 can be any standard cylindrical battery, such as quadruple-A, triple-A, or double-A, or a battery from the family of button cell and coin cell batteries. A specific example of a battery 228 is the CR2450 coin cell 3-volt battery with 600 mAh capacity.

The communications interface 210 may be any wired and/or wireless communication interface for connecting to a network (not shown) and by which information may be exchanged with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Wi-Fi, Wi-Max, IEEE 402.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. Examples of information facilitated by the communications interface 210 include the transmission of the dosing regimen 214 and the actual dose information 218. Other examples of information facilitated by the communications interface 210 is the transmission of a "missed dose" alert and an "extra dose" alert to the patient, clinician, or caregiver, or other authorized stakeholder.

In another example, the communications interface 210 can include a cellular radio. The presence of the cellular radio in the data-enabled syringe collection container 100 allows the container to communicate directly through a cellular network (see FIG. 20) in the absence of any other intermediary devices, such as a smartphone or tablet device. In one example, the cellular radio can be based on the 4G-LTE SocketModem Cell embedded cellular modems available from Multi-Tech Systems, Inc. (Mounds View, Minn.). In another example, the cellular radio can be based on the baseband chipset and/or the radio transceiver products, including GSM, GPRS, EDGE, WCDMA, and TD-SCDMA chipsets, available from MediaTek, Inc. (Hsinchu City, Taiwan). In yet another example, the cellular radio can be based on the Othello® radio and SoftFone® baseband chipsets and/or the cellular handset baseband chipsets available from Analog Devices, Inc. (Norwood, Mass.).

The processor 212 is used to manage the overall operations of the data-enabled syringe collection container 100 with respect reminding at dose time, then tracking and communicating valid dose events and/or missed dose events as well as related events and messages. The processor 212 can be any standard controller or microprocessor device that is capable of executing program instructions. A certain amount of data storage (not shown) may be associated with the processor 212.

Using the communications interface 210, a patient's dosing regimen 214 can be loaded into the processor 212. The dosing regimen 214 can be any information about the patient's medication and prescribed dosing regimen. In one example, the patient's dosing regimen 214 indicates one self-inject dose per day of a certain medication. In another example, the patient's dosing regimen 214 indicates one self-inject dose every three days of a certain medication. In another example, the patient's dosing regimen 214 indicates one self-inject dose per week of a certain medication.

The dose detection algorithm 216 that is programmed into the processor 212 is used to detect valid dose events. In one example, a dose event is deemed valid based on sensing that both the container lid 130 and the trapdoor 137 are open at substantially the same time. In another example, a dose event is deemed valid based on (1) sensing that both the container lid 130 and the trapdoor 137 are open at substantially the same time, and (2) sensing that the amount of time that the trapdoor 137 is open corresponds to an expected amount of time that it takes for a spent syringe to pass through the trapdoor 137. That is, because a syringe is an elongated item of known size, it can be predetermined approximately how much time (e.g., about 0.75 sec) it takes for a syringe to pass via gravity through the trapdoor 137.

Further, because users may discard other waste items, such as syringe caps, gloves, cotton balls, and sterile wipes, into the data-enabled syringe collection container 100, the detection algorithm 216 may use other qualifying parameters to avoid or entirely eliminate the occurrence of "false" dose events. In one example, if one or more trapdoor open events occur close together in time with a valid dose event, the detection algorithm 216 may determine that waste items other than the spent syringe are being discarded and therefore these trapdoor open events are not registered as valid dose events. In another example, the physical amount that the trapdoor 137 is open (i.e., degree of openness) may be used to assist when determining a valid dose event or not. Again, the amount the trapdoor 137 must open for a syringe to pass therethrough is known. Any other amount, particularly if a lesser amount, can indicate some other waste item being discarded. Further, to help minimize or eliminate other waste items being discarded into the data-enabled syringe collection container 100, "For syringes only" may be marked on the container body 110 and/or on the container lid 130.

In addition to detecting valid dose events, the detection algorithm 216 is used to determine dose exception events with respect to the patient's prescribed medication regimen. Examples of dose exception events may include, but are not limited to, missed doses, extra doses, early doses, and late doses. Other messages such as "Wait for 'Take now' signal," "Check blood pressure," "Set Dr. appointment," also may be signaled.

Again, the tip of the actuation lever 144 protrudes through the upper edge of the data-enabled fitting 120 and engages with the container lid 130. Namely, when the container lid 130 is closed the actuation lever 144 is in one position and when the container lid 130 is open the actuation lever 144 is in another position. For example and referring now to FIG. 14A and FIG. 14B, the actuation lever 144 is an L-shaped member that moves about a pivot point 240. The actuation lever 144 has a lever tip 242 that extends upward and away from the control board 140. The lever tip 242 of the actuation lever 144 may engage with the container lid 130. Additionally, a lower portion of the actuation lever 144 may engage with the pushbutton of the switch 224. Together, the actuation lever 144 and the switch 224 provide the sensing mechanism for determining whether the container lid 130 of the data-enabled syringe collection container 100 is opened or closed.

The actuation lever 144 has two positions. For example, FIG. 14A shows a "Position 1." In "Position 1" the container lid 130 is closed and pressing against the lever tip 242 of the actuation lever 144. In so doing, the lower portion of the actuation lever 144 presses against the pushbutton of the switch 224 (e.g., a momentary contact switch). Accordingly, "Position 1," with the pushbutton of the switch 224 pressed, corresponds to the container lid 130 in the closed state. By contrast, FIG. 14B shows a "Position 2." In "Position 2" the container lid 130 is open and not pressing against the lever tip 242 of the actuation lever 144. In so doing, the lower portion of the actuation lever 144 in not pressed against the pushbutton of the switch 224. Accordingly, "Position 2," with the pushbutton of the switch 224 not pressed, corresponds to the container lid 130 in the open state. In either "Position 1" or Position 2," the detection algorithm 216 logs and timestamps the state of the switch 224, which indicates the closed or open state of the container lid 130.

The data-enabled syringe collection container 100 is not limited to using the actuation lever 114 and the switch 224 for sensing whether the container lid 130 is opened or closed. Other mechanisms can be used. For example, the actuation lever 144 can be omitted and the switch 224 can be installed at the upper edge of the data-enabled fitting 120 such that the container lid 130 can engage directly the pushbutton of the switch 224.

Referring now again to FIG. 13, the trapdoor assembly 134 and/or the control board 140 may include any mechanisms (not shown), such as any sensing devices 225, for determining the closed and open state of the trapdoor 137, for determining the duration that the trapdoor 137 is open, and/or for determining the degree of openness of the trapdoor 137. For example, the control board 140 may include or be in electrical communication with any sensing devices 225, such as other micro-switches (not shown) and/or proximity sensors (not shown), installed with respect to the trapdoor 137.

Still referring to FIG. 13, the processor 212 and/or the dose detection algorithm 216 can be programmed to compare valid dose events that are detected to information stored in the patient's dosing regimen 214. In so doing, it can be determined whether the prescribed dosing regimen is being followed. Namely, using the patient's dosing regimen 214, it can be determined whether self-inject medication doses have been taken on time, whether self-inject medication doses have been missed, whether extra self-inject medication doses have been taken, whether early self-inject medication doses have been taken, and whether late self-inject medication doses have been taken. Additionally, using the patient's dosing regimen 214, the processor 212 and/or the dose detection algorithm 216 can be used to activate reminder indicators and any other types of indicators. Namely, the real-time clock 222 provides a calendar and time of day function that can be used with the dosing regimen 214 in order to determine whether doses have been taken on time, whether doses have been missed, whether extra doses have been taken, whether early doses have been taken, and whether late doses have been taken, and to generate reminders. An example of the real-time clock 222 is the S-35390A, 2-wire CMOS real-time clock, available from Seiko Instruments, Inc (Torrance, Calif.).

The security component 220 in the processor 212 can be any software module that is used to perform any security functions with respect to keeping the contents of, for example, the dosing regimen 214 and the actual dose information 218 secure. For example, the security component 220 may use standard security techniques, such as encryption, secure hashtags (or hash tags), and the like. For example, the security component 220 can be used to decrypt the dosing regimen 214, which may be received encrypted. Additionally, the security component 220 can be used to encrypt the actual dose information 218 when transmitted via communications interface 210. However, the use of encryption in the data-enabled syringe collection container 100 is optional.

The one or more indicators 142 are used to convey information to the patient or caretaker in response to the information processed via processor 212 and/or the dose detection algorithm 216. In one example, the indicators 142 are light-emitting diode (LED) devices. For example, three of the six indicators 142 may be—a green "TAKE" LED, a light green "TAKEN" LED, and a red "MISSED" LED. The remaining three of six indicators may include device status indicators, such as a yellow "CONTAINER FULL" LED, a yellow "CLEAR CONTAINER DOOR" LED, and the like. Further, the remaining three of six indicators may include patient-specific indicators, such as a yellow "CHECK BLOOD PRESSURE" LED, a yellow "MAKE DOCTOR APPOINTMENT" LED, and the like. Further, meaning of each indicator 142 may be printed next to each indicator 142 on the side of the data-enabled fitting 120.

The green "TAKE" LED is used for prompting the user to take the prescribed dose of medication. Whereas oral medication is often to be taken one or more times per day, self-inject medication may be less frequent, such as once per day or once every few days. For example, the information contained within the dosing regimen 214 may indicate a patient should self-inject one dose of medication at 8:00 am every three days. On the first day, when the real-time clock 222 indicates the current time to be 8:00 am, the processor 212 activates the "TAKE" LED. Then on the third day after the previously detected valid dose event, when the real-time clock 222 indicates the current time to be 8:00 am, the processor 212 activates the "TAKE" LED again, and so on.

Upon detecting a valid dose event via dose detection algorithm 216, the "TAKE" LED is deactivated and the light green TAKEN" LED is activated. Namely, the "TAKEN" LED indicates that a valid dose event has occurred as detected via dose detection algorithm 216. For example, if all criteria of the dose detection algorithm 216 are met, the processor 212 activates the "TAKEN" LED. After the valid dose event is detected, the "TAKEN" LED may remain activated (e.g., continues to flash) for some period of time (e.g., an hour or until the next dose time).

The red "MISSED" LED indicates a user has not taken the dose of medication in accordance to the dosing regimen 214. Using the real-time clock 222, the processor 212 may be programmed to activate the "MISSED" LED, for example, one hour past the scheduled dose time. For example, the information contained within the dosing regimen 214 may indicate a patient should take the dose at 8:00 am. In this example, when the real-time clock 222 indicates the current time is 9:00 am and a dose event has not recently been detected via dose detection algorithm 216, the processor 212 activates the "MISSED" LED. The "MISSED" LED may remain activated for a predetermined period of time (e.g., 1 hour) or until the "TAKE" LED is next activated. Additionally, using the communications interface 210, a "missed dose" alert can be transmitted to the patient, caretaker, or any other authorized party.

In another example, the yellow "CLEAR CONTAINER DOOR" LED may indicate, for example, that the trapdoor 137 may be stuck open and needs to be cleared. Additionally, using the communications interface 210, a "clear container door" alert can be transmitted to the patient, caretaker, or any other authorized party.

In yet another example and based on a count of valid dose events, the yellow "CONTAINER FULL" LED may indicate that the data-enabled syringe collection container 100 is full and needs to be turned in and exchanged for an empty data-enabled syringe collection container 100. Additionally, using the communications interface 210, a "container full" alert can be transmitted to the patient, caretaker, or any other authorized party.

FIG. 15 illustrates a perspective view of an example of a standard syringe collection container 300 that is not data-enabled. The standard syringe collection container 300 includes a container body 310 and a container inlet 312 that has a removable container lid 314. The container body 310 is substantially the same as the container body 110 of the data-enabled syringe collection container 100. Accordingly, in some embodiments, the standard syringe collection container 300 can be retrofitted to form the data-enabled syringe collection container 100. For example, the data-enabled syringe collection container 100 can be formed by removing the container inlet 312 of the standard syringe collection container 300 and then installing the data-enabled fitting 120 atop the container body 310 of the standard syringe collection container 300.

FIG. 16, FIG. 17, and FIG. 18 show photos of another example of the presently disclosed data-enabled syringe collection container; namely, a data-enabled syringe collection container 400. In this example, the data-enabled syringe collection container 400 includes four indicators 142 instead of six.

Referring again to FIG. 1 through FIG. 18, the operation of the data-enabled syringe collection container 100 can be summarized as follows. The dose detection algorithm 216 is used to detect valid dose events. In one example, by monitoring the states of the switch 224 (indicating the state of the container lid 130), the sensing devices 225 (indicating the state of the trapdoor 137), and the real-time clock 222, if the dose detection algorithm 216 detects that both the container lid 130 and the trapdoor 137 are open at substantially the same time, then a time-stamped valid dose event is logged in the actual dose information 218.

In another example, by monitoring the states of the switch 224 (indicating the state of the container lid 130), the sensing devices 225 (indicating the state of the trapdoor 137), and the real-time clock 222, if the dose detection algorithm 216 detects (1) that both the container lid 130 and the trapdoor 137 are open at substantially the same time and (2) that the amount of time that the trapdoor 137 is open corresponds to an expected amount of time that it takes for a spent syringe to pass through the trapdoor 137, then a time-stamped valid dose event is logged in the actual dose information 218.

The valid dose events that are detected can be compared to information in the patient's dosing regimen 214 in order to determine whether the prescribed dosing regimen is being followed. Namely, using the patient's dosing regimen 214, it can be determined whether the self-inject medication doses are taken on time, whether doses have been missed, whether extra doses have been taken, whether early doses have been taken, and/or whether late doses have been taken. Additionally, using the patient's dosing regimen 214 and the dose detection algorithm 216, the processor 212 can be used to activate any of the indicators 142. Further, the time-stamped states of any of the indicators 142 can be logged in the actual dose information 218.

Figure 19:
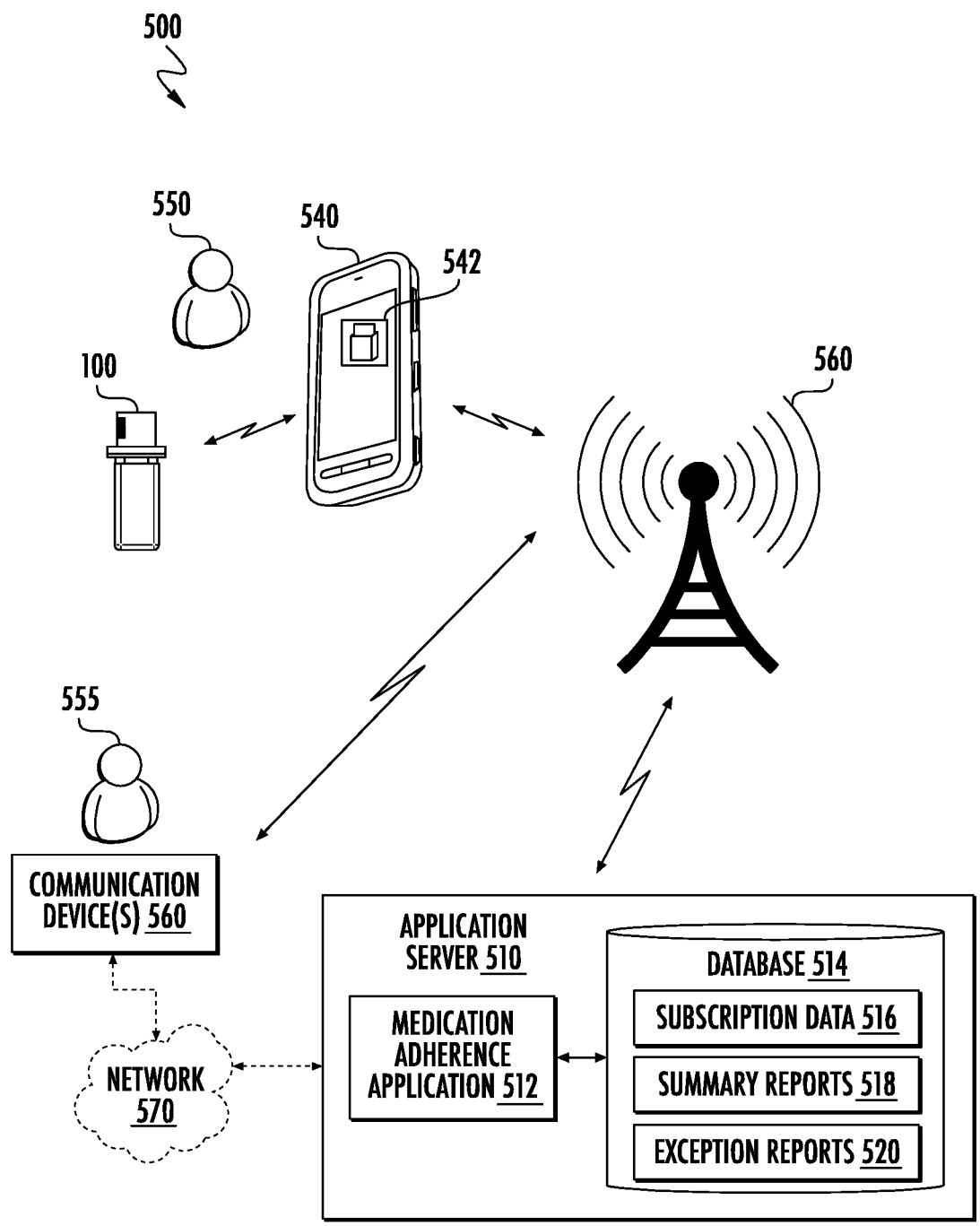
Figure 20:
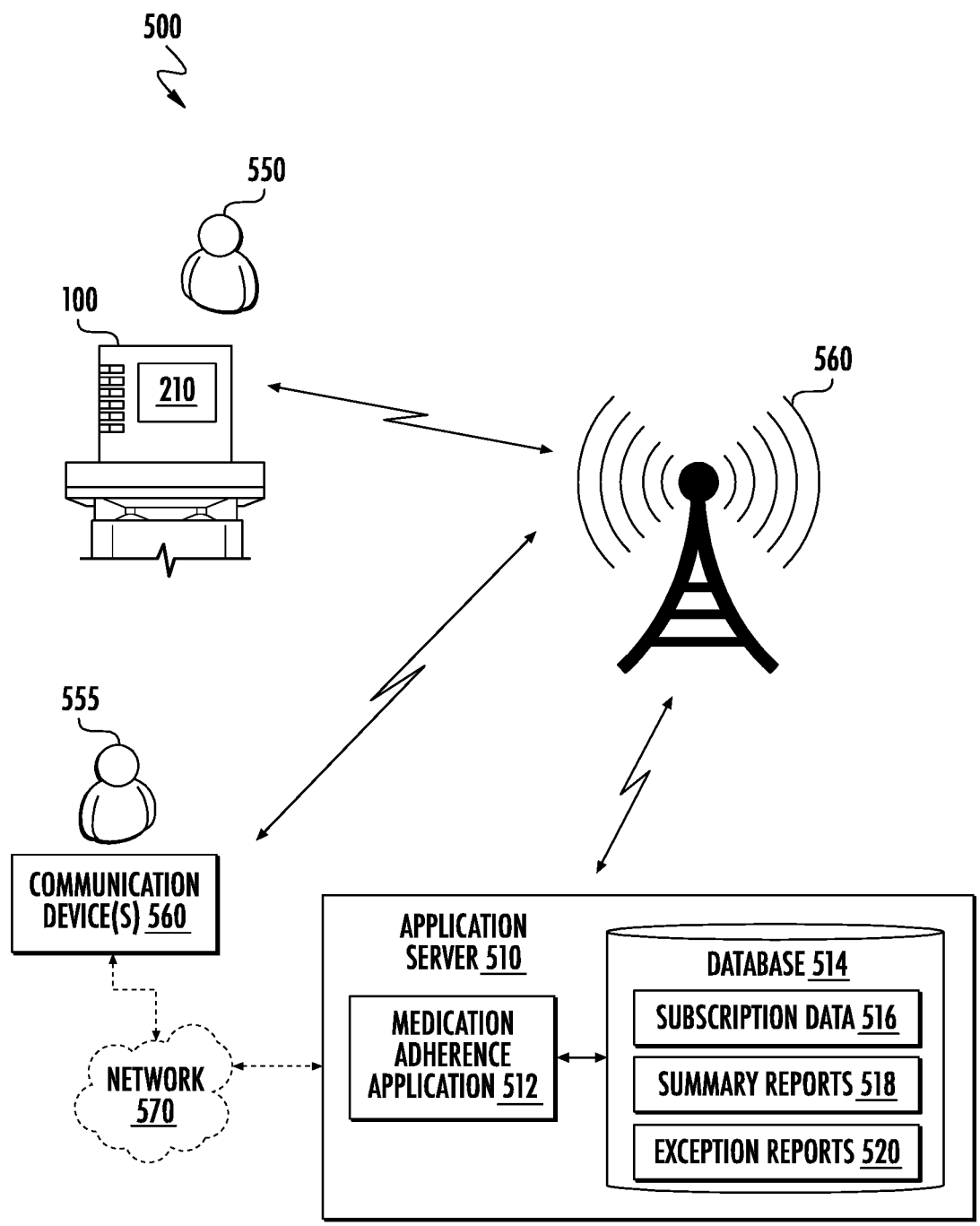

FIG. 19, FIG. 20, FIG. 21, and FIG. 22 below show block diagrams of examples of medication adherence systems that include the presently disclosed data-enabled syringe collection containers 100. Namely, FIG. 19 and FIG. 20 show a medication adherence system 500, FIG. 21 shows a medication adherence system 600, and FIG. 22 shows a medication adherence system 700. In one example, the medication adherence systems 500, 600, 700 can be based on the medication adherence systems that are described with reference to U.S. Patent Pub. No. 20140052468 and U.S. Patent Pub. No. 20150254427, both entitled "Medication Adherence System for and Method of Monitoring a Patient Medication Adherence and Facilitating Dose Reminders."

Referring now to FIG. 19 is a block diagram of the medication adherence system 500 that includes the presently disclosed data-enabled syringe collection container 100 for monitoring a patient's medication adherence with respect to self-inject medications and facilitating dose-reminder and/or dose-taken notifications. In medication adherence system 500, communication is facilitated primarily via the cellular network.

The medication adherence system 500 includes an application server 510. The application server 510 can be any centralized server or computer that is accessible via a network. In one example, the application server 510 is a cloud server. Residing at the application server 510 is a medication adherence application 512 and a database 514. Stored at the database 514 are, for example, subscription data 516, summary reports 518, and exception reports 520.

The medication adherence system 500 also includes one or more data-enabled syringe collection containers 100. Each of the data-enabled syringe collection containers 100 includes mechanisms for reminding at dose time, then tracking and communicating valid dose events, as well as missed, extra, early, and/or late dose events as well as related events and messages. Each of the data-enabled syringe collection containers 100 includes control electronics for processing and communicating information about valid dose events, missed dose events, and/or extra dose events as well as related events and messages. In one example, a dose event is deemed valid based on sensing that both the container lid 130 and the trapdoor 137 are open at substantially the same time. In another example, a dose event is deemed valid based on (1) sensing that both the container lid 130 and the trapdoor 137 are open at substantially the same time, and (2) sensing that the amount of time that the trapdoor 137 is open corresponds to an expected amount of time that it takes for a spent syringe to pass through the trapdoor 137.

The medication adherence system 500 also includes a mobile phone 540. The mobile phone 540 can be any smartphone that is capable of (1) running mobile applications and (2) communicating with the data-enabled syringe collection container 100. The mobile phone 540 can be, for example, an Android™ phone, an Apple iPhone, a Samsung Galaxy phone, a Google phone, and the like. The mobile phone 540 can also be any other mobile device that has cellular network capability, such as a cellular-enabled tablet device (e.g., the 3G or 4G version of the Apple iPad).

In medication adherence system 500, a medication adherence mobile app 542 is running on the mobile phone 540. The medication adherence mobile app 542 is the counterpart to the medication adherence application 512 that is running at the application server 510. The data-enabled syringe collection container 100 and the mobile phone 540 belong to a patient 550 that is associated with the medication adherence system 500.

In the medication adherence system 500, the patient 550's data-enabled syringe collection container 100 can transmit information wirelessly to the patient's mobile phone 540. Then, the patient's mobile phone 540 is used to transmit (via a cellular network 560) the patient-specific information to the application server 510, wherein the application server 510 is used for collecting and processing patient-specific information from the data-enabled syringe collection container 100.

The medication adherence system 500 is not limited to one patient 550 and his/her one data-enabled syringe collection container 100 and one mobile phone 540. The medication adherence system 500 can support any number of patients 550, data-enabled syringe collection containers 530, and mobile phones 540, wherein the application server 510 collects and processes patient-specific information from multiple patients 550. Further, any given patient 550 can have multiple data-enabled syringe collection containers 530, which correspond to multiple medication prescriptions. In one example, the medication adherence system 500 can be implemented in a client-server type of system architecture, wherein the mobile phones 540 are the clients and the application server 510 is the server.

Further, the medication adherence system 500 can be a subscription-based system, wherein patients 550 subscribe to the medication adherence system 500 in order to download the medication adherence mobile app 542 to their mobile phones 540 and to take advantage of the functionality of the medication adherence application 512 at application server 510. The subscription data 516 in the database 514 at the application server 510 may contain, for example, patient names, patient account information, patient credentials, patient profiles, a record of the patient's prescriptions, and the like. The exception reports 520 in the database 514 are patient-specific exception information, wherein examples of exceptions include, but are not limited to, missed doses, extra doses, early doses, and late doses. The medication adherence application 512 determines patient-specific exceptions and generates patient-specific summary reports 518 by analyzing patient-specific information that is generated at each patient 550's data-enabled syringe collection container 100 and then transmitted to application server 510 via each patient 550's mobile phone 540.

Associated with the medication adherence system 500 are one or more notifiers 555. In one example, when an exception occurs (e.g., missed, extra, early, or late dose), notifiers 555 can be any authorized personnel that are tasked to contact the patient 550 and notify them of the exception. Associated with the one or more notifiers 555 are their respective communication devices 560. The communication device 560 is, for example, a mobile phone, a landline phone, or any computing device. For example, using a telephone, a notifier 555 can call a certain patient 550 and notify him/her that a dose of medication was recently missed, thereby providing a reminder to get caught up on his/her dosing regimen. In another example, exception notifications can be transmitted electronically to the patient 550, such as via email or text message. The communication devices 560 of the notifiers 555 can be connected to the application server 510 via the cellular network 560 or optionally via a network 570. The network 570 can be any network for providing wired or wireless connection to the Internet, such as a local area network (LAN) or a wide area network (WAN).

Referring now to FIG. 20, in another embodiment of the medication adherence system 500, when the communications interface 210 of the data-enabled syringe collection container 100 includes the cellular radio, the data-enabled syringe collection container 100 may communicate directly to the application server 510 without the use of the mobile phone 540. Accordingly, in this example, the medication adherence system 500 is absent the mobile phones 540.

Referring now to FIG. 21 is a block diagram of the medication adherence system 600 that includes the presently disclosed data-enabled syringe collection container 100 for monitoring a patient's medication adherence with respect to self-inject medications and facilitating dose-reminder and/or dose-taken notifications. In medication adherence system 600, communication is facilitated primarily via the Internet.

The medication adherence system 600 is substantially the same as the medication adherence system 500 of FIG. 19, except that the cellular network 560 is replaced with the network 570. Further, the mobile phones 540 with their medication adherence mobile apps 542 are replaced with computing devices 640, wherein each of the computing devices 640 has a mobile/desktop medication adherence application 642 running thereon. The computing devices 640 can be, for example, desktop computers, laptop computers, handheld computing devices, smartphones, smartwatches, personal digital assistants (PDAs), and tablet devices. The computing devices 640 have wireless communication capabilities for communicating with the data-enabled syringe collection containers 530. For example, the computing device 640 is Bluetooth®-enabled and/or Wi-Fi-enabled for communicating wirelessly with other local devices, such as the data-enabled syringe collection container 100. The computing device 640 can be, for example, an Apple iPad.

Like the medication adherence mobile app 542 of FIG. 19, the mobile/desktop medication adherence application 642 is the counterpart to the medication adherence application 512 that is running at the application server 510.

Referring now to FIG. 22 is a block diagram of the medication adherence system 700 that includes the presently disclosed data-enabled syringe collection container 100 for monitoring a patient's medication adherence with respect to self-inject medications and facilitating dose-reminder and/or dose-taken notifications. In medication adherence system 700, communication is facilitated primarily via a landline.

The medication adherence system 700 is substantially the same as the medication adherence system 500 of FIG. 19, except that the mobile phones 540 and the cellular network 560 are replaced with a Bluetooth landline (or dial-up) modem 710 and the application server 510 is a dial-in server. The Bluetooth landline (or dial-up) modem 710 provides both landline dial-up capability for communicating with the dial-in application server 510 and Bluetooth technology for communicating with the data-enabled syringe collection container 100. Examples of the Bluetooth landline (or dial-up) modem 710 include, but are not limited to, the Sitecom CN-503 Bluetooth Modem available from Sitecom Europe BV (Rotterdam, Zuid-Holland) and the Model 4300 Zoom Bluetooth Modem available from Zoom Telephonics Inc. (Boston, Mass.).

In the medication adherence system 700, the processor 512 may be programmed to transmit the actual dose information 518 and optionally the dosing regimen 514 to the dial-in application server 510 once per day, such as at midnight. For example, the data-enabled syringe collection container 100 communicates via Bluetooth technology with the Bluetooth landline (or dial-up) modem 710 to initiate a dial-up operation, then transmits the contents of the actual dose information 518 and optionally the dosing regimen 514 to the dial-in application server 510 over a landline.

FIG. 23 illustrates a block diagram of another configuration of the control board 140 of the presently disclosed data-enabled syringe collection container 100, wherein the configuration supports remote processing capability rather than onboard processing capability. Namely, whereas previously certain processing capability is provided onboard the data-enabled syringe collection container 100 via the patient's dosing regimen 214, the dose detection algorithm 216, the actual dose information 218, and optionally the security component 220 installed and running locally on the processor 212 of the control board 140, in this example this processing capability is done remotely of the data-enabled syringe collection container 100. For example, the patient's dosing regimen 214, the dose detection algorithm 216, the actual dose information 218, and optionally the security component 220 is installed and running remotely on, for example, the medication adherence mobile app 542 of the mobile phones 540 or the mobile/desktop medication adherence application 642 of the computing devices 640.

In this example, the processor 212 on the control board 140 simply communicates the states of, for example, the switch 224 and the sensing devices 225 to the medication adherence mobile app 542 and/or the mobile/desktop medication adherence application 642. Then, the medication adherence mobile app 542 and/or the mobile/desktop medication adherence application 642 processes the information and returns information to the data-enabled syringe collection container 100 for controlling the indicators 142 with respect to dose-reminder and/or dose-taken notifications and any other notifications.

Example embodiments may be described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), microcontroller or graphics processing unit.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. In the drawings and specification, there have been disclosed typical preferred embodiments of the invention and, although specific terms are employed, they are used in a generic and descriptive sense only and not for purposes of limitation, the scope of the invention being set forth in the following claims.

We claim:

1. A data-enabled syringe collection container, comprising:
   a) an upper inlet body, comprising: an inlet lid; a first opening; an entry channel; and a receiving assembly, wherein the inlet lid is configured for covering and accessing the first opening and the entry channel is configured to provide a passageway from the first opening to the receiving assembly, and wherein the receiving assembly comprises a dropout door configured to allow passage through a second opening into the container body;
   b) a container body coupled to the upper inlet body; and
   c) an electronics module configured for sensing and tracking dose events, the electronics module coupled to at least one of the upper inlet body and the container body.

2. The container of claim 1 wherein the dropout door comprises a spring-loaded one-way door configured to open downward into the container body and to automatically close after an article has passed through.

3. The container of claim 1 wherein the entry channel is tapered from a top portion to a bottom portion thereof.

4. The container of claim 1 wherein the container body is configured as a reservoir for holding a quantity of spent syringes.

5. The container of claim 1 wherein the first opening, the entry channel, and the second opening are configured to allow for a syringe to pass there through.

6. The container of claim 1 wherein the electronics module comprises a control board.

7. The container of claim 6 wherein the control board comprises one or more active and passive electrical and/or mechanical components for sensing one or more of when the inlet lid and/or dropout door is open and closed, a duration and time that the inlet lid and/or dropout door is open, and a physical amount that the inlet lid and/or dropout door is open.

8. The container of claim 7 wherein the control board, comprises a processor configured for processing data from the one or more active and passive electrical and/or mechanical components with respect to a patient's dosing regimen and for storing and/or communicating information generated from the processed data.

9. The container of claim 6 wherein the control board comprises any one or more of a communications interface, a processor, a real-time clock, one or more switches, one or more sensors, and one or more indicators.

10. The container of claim 9 wherein the one or more indicators comprise one or more light-emitting diodes (LEDs).

11. The container of claim 9 wherein the processor comprises data storage for storing one or more of a patient's dosing regimen, a dose detection algorithm, actual dose data, and a security component, wherein the processor is configured to process data from one or more of the real-time clock, the one or more switches, and/or the one or more sensors with respect to a patient's predefined dosing regimen, and for one or more of storing and communicating data about doses taken, doses missed, extra doses, early doses, and/or late doses.

12. The container of claim 9 wherein one or more of the real-time clock, the one or more switches, and/or the one or more sensors are configured to detect one or more of the open or closed state, the time and duration opened, and the degree of openness of one or both of the inlet lid and the dropout door.

13. The container of claim 12 wherein a dose event is deemed valid if it is detected that both the inlet lid and the dropout-door are opened and/or closed at substantially the same time.

14. The container of claim 12 wherein a dose event is deemed valid if it is detected that both the inlet lid and the dropout-door are open at substantially the same time and any one or more of: that the amount of time that the dropout door is open corresponds to a predefined amount of time; the degree of openness of the dropout door meets a predefined threshold value; and that a time period between successive dropout door openings is greater than a predefined minimum threshold of time.

15. The container of claim 14 wherein the predefined amount of time that the dropout door is open is substantially equal to an amount of time that it takes for a spent syringe to pass through the dropout door.

16. The container of claim 7 wherein one of the one or more active and passive electrical and/or mechanical components comprises a movable lever.

17. The container of claim 16 wherein a portion of the movable lever extends through a corresponding opening in an upper edge of the upper inlet body and is configured to engage with the inlet lid, wherein the movable lever is part of a mechanism for detecting an open or closed state of the inlet lid.

18. The container of claim 17 wherein the movable lever is configured such that when the inlet lid is closed the inlet lid is in contact with the movable lever causing the movable lever to be in a first position, and when the inlet lid is open the inlet lid does not contact the movable lever causing the movable lever to be in a second position.

19. The container of claim 18 wherein the one or more active and passive electrical and/or mechanical components further comprise a momentary contact switch and wherein the movable lever in one of the first and second positions engages an actuator of the momentary contact switch.

20. The container of claim 19 wherein the movable lever and the momentary contact switch provide the mechanism for determining whether the inlet lid is in an opened or closed state, wherein when the inlet lid is closed and in contact with the tip of the movable lever, a portion of the movable lever is pushed against the actuator of the momentary contact switch, and the momentary contact switch is in one state, and when the inlet lid is open and not in contact with the tip of the movable lever, the movable lever is not pushed against the actuator of the momentary contact switch, and the momentary contact switch is in another state.

21. The container of claim 1 wherein the electronics module is configured for providing one or more of a reminder at dose time, detecting valid dose events, and processing and communicating data about dose events and/or dose exception events.

22. The container of claim 9 wherein sensing a valid dose event requires data input from at least two of the one or more switches and/or one or more sensors to coincide with one another.

23. The container of claim 22 wherein the coinciding at least two data inputs from the one or more switches and/or one or more sensors comprises data input indicating the inlet lid and the dropout door are open at substantially the same time.

24. The container of claim 21 wherein the electronics module is configured for transmitting data therefrom via a communications interface to an external computing device via a wired and/or wireless network to one or more of a patient, a caretaker, and/or an authorized party via the communications interface, wherein the data comprises information regarding an actual dose event.

25. The container of claim 24 wherein if the information regarding the actual dose event indicates a missed dose according to a patient's dosing regimen the electronics module is configured to activate one or more indicators to indicate a missed dose, and wherein if the information regarding the actual dose event indicates a valid dose event according to the patient's dosing regimen the electronics module is configured to activate one or more indicators to indicate a taken dose.

26. The container of claim 24 wherein the electronics module is further configured to determine whether a prescription refill is needed based on a number of valid dose events as compared to recorded actual dose data and a patient's dosing regimen, and wherein if it is determined a prescription refill is needed the electronics module is configured to activate one or more indicators to indicate a prescription refill is needed, and further wherein a prescription refill notice may be sent to one or more of to one or more of a patient, a caretaker, and/or an authorized party via the communications interface.

27. A data-enabled device for receiving spent syringes, comprising:
a) an inlet body, comprising:
   (i) an inlet lid;
   (ii) a first opening;
   (iii) an entry channel;
   (iv) a receiving assembly; and
   wherein the inlet lid is configured for covering and accessing the first opening, and wherein the entry channel is configured to provide a passage way from the first opening to the receiving assembly, and wherein the receiving assembly comprises a dropout door configured to allow passage through a second opening, and further wherein the first opening, the entry channel, the receiving assembly, and the second opening are configured to allow a spent syringe to pass there through; and
b) an electronics module configured for sensing and tracking dose events, the electronics module coupled to the inlet body.

* * * * *